United States Patent
Harris et al.

(10) Patent No.: US 10,577,594 B2
(45) Date of Patent: Mar. 3, 2020

(54) POLYPEPTIDES HAVING ARABINOFURANOSIDASE ACTIVITY AND POLYNUCLEOTIDES ENCODING SAME

(71) Applicant: Novozymes, Inc., Davis, CA (US)

(72) Inventors: Paul Vincent Harris, Carnation, WA (US); Sumati Hasani, Danville, CA (US); Fang Liu, Livermore, CA (US)

(73) Assignee: Novozymes, Inc., Davis, CA (US)

( * ) Notice: Subject to any disclaimer, the term of this patent is extended or adjusted under 35 U.S.C. 154(b) by 2 days.

(21) Appl. No.: 15/746,974

(22) PCT Filed: Jul. 22, 2016

(86) PCT No.: PCT/US2016/043521
§ 371 (c)(1),
(2) Date: Jan. 23, 2018

(87) PCT Pub. No.: WO2017/019490
PCT Pub. Date: Feb. 2, 2017

(65) Prior Publication Data
US 2019/0010472 A1    Jan. 10, 2019

Related U.S. Application Data

(60) Provisional application No. 62/196,540, filed on Jul. 24, 2015.

(51) Int. Cl.
*C12N 1/20* (2006.01)
*C12N 9/24* (2006.01)
*C12N 15/52* (2006.01)
*C12N 15/82* (2006.01)

(52) U.S. Cl.
CPC ........... *C12N 9/2402* (2013.01); *C12N 15/52* (2013.01); *C12N 15/8257* (2013.01); *C12Y 302/01* (2013.01); *C12Y 302/01055* (2013.01); *C07K 2319/00* (2013.01); *C07K 2319/01* (2013.01)

(58) Field of Classification Search
CPC ...................... C12Y 302/01055; C12N 9/2402
See application file for complete search history.

(56) References Cited

U.S. PATENT DOCUMENTS

2005/0202528 A1    9/2005   Blondelet-Rouault et al.

FOREIGN PATENT DOCUMENTS

| | | |
|---|---|---|
| CN | 103865867 | 6/2014 |
| KR | 20130012708 | 2/2013 |
| WO | 2009073383 A1 | 6/2009 |

OTHER PUBLICATIONS

Fischbach et al, 2010, UniProt Access No. D9Y0M4.
Jankowitsch et al, 2013, UniProt Access No. K4QV65.
Wang et al, 2016, UniProt Access No. A0A170X5U9.

*Primary Examiner* — Tekchand Saidha
(74) *Attorney, Agent, or Firm* — Robert Starnes

(57) ABSTRACT

The present invention relates to isolated polypeptides having arabinofuranosidase activity, catalytic domains, carbohydrate binding modules and polynucleotides encoding the polypeptides, catalytic domains or carbohydrate binding modules. The invention also relates to nucleic acid constructs, vectors, and host cells comprising the polynucleotides as well as methods of producing and using the polypeptides, catalytic domains or carbohydrate binding modules.

25 Claims, 4 Drawing Sheets
Specification includes a Sequence Listing.

SEQUENCE LISTING

```
<160> NUMBER OF SEQ ID NOS: 10

<210> SEQ ID NO 1
<211> LENGTH: 912
<212> TYPE: DNA
<213> ORGANISM: Actinomadura rubrobrunea

<400> SEQUENCE: 1
ccgacgtgcg acctcccgtc gacgtaccgc tggacgtcga cgggcccgct ggcgcagccg    60
aaggcgggat gggtctcgct caaggacttc accgtcgccc cctacaacgg aaagcacctc   120
gtctacgcga cgactcacga cacgggcacc aggtggggtt cgatgaactt cagcccgttc   180
ggcgactggt cggagatggc ctacgccagc cagaacgcga tgacgaacgc cgccgtcgcg   240
cccacgctgt tctacttcgc gccgaagaac atctgggtgc tcgcctacca gtggggacgc   300
accgccttct cctaccgcac gtcgaccgac cccaccaacc cgaacggctg gtcggcggag   360
caggagctct tctccgggag catctccggc tccccgacgg gtcccatcga ccagacgctc   420
atcgccgacg acacgaccat gtacctgttc ttcgccggtg acaacgggaa gatctaccgg   480
gccagcatgc cgatcggcga gttcccgcgc agcttcggca cggcctcgac ggtggtcatg   540
agcgactcga cgaacaacct gttcgaagcc gttcaggtct acaagctcca aggccagaac   600
cgctacctca tgctcgtcga ggcgatcggt tcgcagggac gctacttccg ctcgttcacg   660
gccaccagcc tgaacgggtc gtggacgccg caggccgcga ccgagagcaa ccccttcgcc   720
ggcaaggcca acagcggcgc cacgtggacc aacgacatca gccacggcga actggtccgc   780
acgagcgccg accagacctt caccgtggac ccctgcaacc tgcagctgct ctaccagggc   840
cgcgacccca actccggcgg cgactacggc ctcctgccct accggccggg tctgctgacg   900
ctccagcgct ga                                                       912

<210> SEQ ID NO 2
<211> LENGTH: 303
<212> TYPE: PRT
<213> ORGANISM: Actinomadura rubrobrunea

<400> SEQUENCE: 2

Pro Thr Cys Asp Leu Pro Ser Thr Tyr Arg Trp Thr Ser Thr Gly Pro
1               5                   10                  15

Leu Ala Gln Pro Lys Ala Gly Trp Val Ser Leu Lys Asp Phe Thr Val
                20                  25                  30

Ala Pro Tyr Asn Gly Lys His Leu Val Tyr Ala Thr Thr His Asp Thr
            35                  40                  45

Gly Thr Arg Trp Gly Ser Met Asn Phe Ser Pro Phe Gly Asp Trp Ser
        50                  55                  60

Glu Met Ala Tyr Ala Ser Gln Asn Ala Met Thr Asn Ala Ala Val Ala
65                  70                  75                  80

Pro Thr Leu Phe Tyr Phe Ala Pro Lys Asn Ile Trp Val Leu Ala Tyr
                85                  90                  95
```

```
Gln Trp Gly Arg Thr Ala Phe Ser Tyr Arg Thr Ser Thr Asp Pro Thr
                100                 105                 110

Asn Pro Asn Gly Trp Ser Ala Glu Gln Glu Leu Phe Ser Gly Ser Ile
        115                 120                 125

Ser Gly Ser Pro Thr Gly Pro Ile Asp Gln Thr Leu Ile Ala Asp Asp
    130                 135                 140

Thr Thr Met Tyr Leu Phe Phe Ala Gly Asp Asn Gly Lys Ile Tyr Arg
145                 150                 155                 160

Ala Ser Met Pro Ile Gly Glu Phe Pro Arg Ser Phe Thr Ala Ser
                165                 170                 175

Thr Val Val Met Ser Asp Ser Thr Asn Asn Leu Phe Glu Ala Val Gln
                180                 185                 190

Val Tyr Lys Leu Gln Gly Gln Asn Arg Tyr Leu Met Leu Val Glu Ala
        195                 200                 205

Ile Gly Ser Gln Gly Arg Tyr Phe Arg Ser Phe Thr Ala Thr Ser Leu
    210                 215                 220

Asn Gly Ser Trp Thr Pro Gln Ala Ala Thr Glu Ser Asn Pro Phe Ala
225                 230                 235                 240

Gly Lys Ala Asn Ser Gly Ala Thr Trp Thr Asn Asp Ile Ser His Gly
                245                 250                 255

Glu Leu Val Arg Thr Ser Ala Asp Gln Thr Phe Thr Val Asp Pro Cys
                260                 265                 270

Asn Leu Gln Leu Leu Tyr Gln Gly Arg Asp Pro Asn Ser Gly Gly Asp
        275                 280                 285

Tyr Gly Leu Leu Pro Tyr Arg Pro Gly Leu Leu Thr Leu Gln Arg
    290                 295                 300

<210> SEQ ID NO 3
<211> LENGTH: 1428
<212> TYPE: DNA
<213> ORGANISM: Streptomyces thermoalcalitolerans

<400> SEQUENCE: 3
atgcacacag gacgtttcag ccgaaggcat ccgtccgcgg tgctcgccgc cgcggtcgcg      60
gtcctggccg cattggcggc catgctcgcg gccaccccgg cccaggccgc ttccaccggt     120
tcattacgcg gtgtcggttc gaaccgatgc ctcgatgtgc cgggcgccag ccaggccaac     180
ggcacatatc tgcagatcta cgactgctgg ggcgggacca ccagcagtg dacgctgacg      240 gacagcaacc agctcaccgt gtacggcgac aagtgcctgg atgttccggg ccatgccacc     300
acggccggta cccgggtgca gatctggacc tgttccggcg gtgcgaacca gcagtggcgg     360
gtcaactccg acggcacggt cgtcggcgtg cagtccgggc tgtgcctgga ggccgcgggc     420
gccggtacgg ccaacggcac agcagtgcag atcgggacgt gcaacggcgg cagccaccag     480
aagtggaccg gcctgcccgg gaccccgact cagcccggcg acacgtgctc ccttccgtcg     540
acgtaccggt ggacctcgac gggtgcgctg gcgcagccgg cgaacggatg gtctcgctg     600 aaggacttca ccgccgtgaa gcacaacggc aagtacctgg tctacgggtc gaacttctcg     660
ggatcgtcgt acggctcgat gatgttcagc cccttcacga actggtcgga catggcatcg     720
gcccgccagc tcgggatgaa ccaggccgcg gtggcgccca cgctgttcta cttcgcgccc     780
aagaacatat gggtgctggc gtaccagtgg ggtgcgtggc ccttcgtcta ccgcacgtcg     840 agcgaccccca ccgacccccaa cggctggtcc gccccgcagc cgctgttcac cgggagcatt     900
cccgactccg acaccggccc gatcgaccag accctgatcg ccgacgaccg gaacatccac     960
```

-continued

```
ctgttcttcg ccggtgacaa cggcaggatc taccgcgcga gcatgccgat cgggaacttc   1020
ccgggcaact tcggctcgtc gtacacgacg atcatgagcg acacgaaggc caacctcttc   1080
gagggcgtac aggtctacaa ggtcaagggc cagaaccagt acctcatgat cgtcgaggcg   1140 atggggcga acgggcgcta cttccgttcc ttcacggcct ccagcctgag cggctcgtgg    1200
accccgcagg ccgccaccga gagcaacccc ttcgcgggca aggccaacag cggcgccacc   1260
tggaccaacg acatcagcca cggcgacctg gtccgcgaca ccccgaccga gaccatgacc   1320
gtcgaccccc tgcaatctgca gttcctctac cagggcaagt ccccaccgc gggcggcgac    1380 tacaaccgac tgccgtggcg gccgggtgtc ctcaccctgc agcgctga             1428
```

<210> SEQ ID NO 4
<211> LENGTH: 475
<212> TYPE: PRT
<213> ORGANISM: Streptomyces thermoalcalitolerans

<400> SEQUENCE: 4

```
Met His Thr Gly Arg Phe Ser Arg Arg His Pro Ser Ala Val Leu Ala
 1               5                  10                  15

Ala Ala Val Ala Val Leu Ala Ala Leu Ala Ala Met Leu Ala Ala Thr
            20                  25                  30

Pro Ala Gln Ala Ala Ser Thr Gly Ser Leu Arg Gly Val Gly Ser Asn
        35                  40                  45

Arg Cys Leu Asp Val Pro Gly Ala Ser Gln Ala Asn Gly Thr Tyr Leu
    50                  55                  60

Gln Ile Tyr Asp Cys Trp Gly Gly Thr Asn Gln Gln Trp Thr Leu Thr
65                  70                  75                  80

Asp Ser Asn Gln Leu Thr Val Tyr Gly Asp Lys Cys Leu Asp Val Pro
                85                  90                  95

Gly His Ala Thr Thr Ala Gly Thr Arg Val Gln Ile Trp Thr Cys Ser
            100                 105                 110

Gly Gly Ala Asn Gln Gln Trp Arg Val Asn Ser Asp Gly Thr Val Val
        115                 120                 125

Gly Val Gln Ser Gly Leu Cys Leu Glu Ala Ala Gly Ala Gly Thr Ala
    130                 135                 140

Asn Gly Thr Ala Val Gln Ile Gly Thr Cys Asn Gly Gly Ser His Gln
145                 150                 155                 160

Lys Trp Thr Gly Leu Pro Gly Thr Pro Thr Gln Pro Gly Asp Thr Cys
                165                 170                 175

Ser Leu Pro Ser Thr Tyr Arg Trp Thr Ser Thr Gly Ala Leu Ala Gln
            180                 185                 190

Pro Ala Asn Gly Trp Val Ser Leu Lys Asp Phe Thr Ala Val Lys His
        195                 200                 205

Asn Gly Lys Tyr Leu Val Tyr Gly Ser Asn Phe Ser Gly Ser Ser Tyr
    210                 215                 220

Gly Ser Met Met Phe Ser Pro Phe Thr Asn Trp Ser Asp Met Ala Ser
225                 230                 235                 240

Ala Arg Gln Leu Gly Met Asn Gln Ala Ala Val Ala Pro Thr Leu Phe
                245                 250                 255

Tyr Phe Ala Pro Lys Asn Ile Trp Val Leu Ala Tyr Gln Trp Gly Ala
            260                 265                 270

Trp Pro Phe Val Tyr Arg Thr Ser Ser Asp Pro Thr Asp Pro Asn Gly
        275                 280                 285

Trp Ser Ala Pro Gln Pro Leu Phe Thr Gly Ser Ile Pro Asp Ser Asp
```

```
                 290                 295                 300
Thr Gly Pro Ile Asp Gln Thr Leu Ile Ala Asp Asp Arg Asn Ile His
305                 310                 315                 320

Leu Phe Phe Ala Gly Asp Asn Gly Arg Ile Tyr Arg Ala Ser Met Pro
                325                 330                 335

Ile Gly Asn Phe Pro Gly Asn Phe Gly Ser Ser Tyr Thr Thr Ile Met
                340                 345                 350

Ser Asp Thr Lys Ala Asn Leu Phe Glu Gly Val Gln Val Tyr Lys Val
            355                 360                 365

Lys Gly Gln Asn Gln Tyr Leu Met Ile Val Glu Ala Met Gly Ala Asn
            370                 375                 380

Gly Arg Tyr Phe Arg Ser Phe Thr Ala Ser Ser Leu Ser Gly Ser Trp
385                 390                 395                 400

Thr Pro Gln Ala Ala Thr Glu Ser Asn Pro Phe Ala Gly Lys Ala Asn
                405                 410                 415

Ser Gly Ala Thr Trp Thr Asn Asp Ile Ser His Gly Asp Leu Val Arg
            420                 425                 430

Asp Asn Pro Asp Gln Thr Met Thr Val Asp Pro Cys Asn Leu Gln Phe
        435                 440                 445

Leu Tyr Gln Gly Lys Ser Pro Thr Ala Gly Asp Tyr Asn Arg Leu
    450                 455                 460

Pro Trp Arg Pro Gly Val Leu Thr Leu Gln Arg
465                 470                 475

<210> SEQ ID NO 5
<211> LENGTH: 906
<212> TYPE: DNA
<213> ORGANISM: Artificial sequence
<220> FEATURE:
<223> OTHER INFORMATION: Synthetic construct

<400> SEQUENCE: 5
ccgacatgcg atctgccgtc aacatataga tggacatcaa caggaccgct ggcacaaccg     60
aaagcaggct gggtttcact gaaagatttt acagttgcac cgtacaatgg caaacatctg    120
gtttatgcaa caacacatga tacaggcaca agatggggct caatgaattt ttcaccgttt    180
ggcgattgga gcgaaatggc atatgcatca caaaatgcaa tgacaaatgc agcagtcgca    240
ccgacactgt tttactttgc accgaaaaac atttgggttc tggcatatca atggggagga    300
acagcatttt catatcgcac aagcacagat ccgacaaatc cgaatggctg gtcagcagaa    360
caagaactgt tttcaggctc aatttcaggc agcccgacag gaccgattga tcaaacactg    420
attgcagatg atacaacgat gtacctgttt tttgcaggcg ataacggcaa aatctataga    480
gcatcaatgc cgattggcga atttccgaga tcatttggca cagcatcaac agttgttatg    540
agcgatagca caaacaacct gtttgaagca gtccaagtct ataaactgca aggccaaaat    600
agatatctga tgctggttga agcaattggc tcacaaggca gatattttag aagctttaca    660
gcgacatcac tgaatggctc atggacaccg caagcagcaa cagaatcaaa tccgtttgca    720
ggcaaagcaa attcaggcgc aacatggaca aatgatattt cacatggcga actggttaga    780
acatcagcgg atcaaacatt tacagtcgat ccgtgcaatc tgcaactgct gtatcaaggc    840
agagatccga attctggcgg agattatggc ctgctgccgt atagaccggg actgctgaca    900
caaaga                                                                906

<210> SEQ ID NO 6
```

```
<211> LENGTH: 46
<212> TYPE: DNA
<213> ORGANISM: Artificial sequence
<220> FEATURE:
<223> OTHER INFORMATION: Synthetic construct

<400> SEQUENCE: 6
gttgctttta gttcatcgat cgcatcggct ccgacatgcg atctgc         46

<210> SEQ ID NO 7
<211> LENGTH: 75
<212> TYPE: DNA
<213> ORGANISM: Artificial sequence
<220> FEATURE:
<223> OTHER INFORMATION: Synthetic Construct

<400> SEQUENCE: 7 gttttttat tgattaacgc gtttagtgat ggtgatggtg atgtgagcca ccgcctcctc    60
tttgtgtcag cagtc                                                   75

<210> SEQ ID NO 8
<211> LENGTH: 1317
<212> TYPE: DNA
<213> ORGANISM: Artificial sequence
<220> FEATURE:
<223> OTHER INFORMATION: Synthetic construct

<400> SEQUENCE: 8
gcatcaacag gctcactgag aggcgttggc tcaaatagat gcctggatgt tcctggcgca    60
tcacaagcaa atggcacata tctgcaaatt tatgattgct ggggtggcac aaatcaacaa   120
tggacactga cagattcaaa tcagctgaca gtttatggcg ataaatgctt agatgttccg   180
ggacatgcaa caacagcagg cacaagagtt caaatttgga catgctcagg cggagcgaat   240
caacagtggc gtgttaattc agatggcaca gttgttggcg ttcaatcagg cctgtgcctg   300
gaagcagcag gcgcaggcac agcaaatgga acagcagtgc aaattggaac atgcaatggc   360
ggatcacatc agaaatggac aggccttccg ggaacaccga cacaacctgg cgatacatgc   420
agcctgccgt caacatatag atggacatct acaggcgcac tggcacaacc ggcaaatggc   480
tgggtttcac tgaaagattt tacagcggtt aaacataacg gcaaatatct ggtttatggc   540
agcaattttt caggctcatc atatggctca atgatgttta gcccgtttac aaattggtca   600
gatatggcat cagcaagaca actgggcatg aatcaagcag cagttgcacc gacactgttt   660
tactttgcac cgaaaaacat tgggttctg gcatatcaat ggggagcatg gccgtttgtt   720
tatagaacat caagcgatcc gacagatccg aatggctggt cagcaccgca accgctgttt   780
acaggctcaa ttccggattc agatacagga ccgattgatc aaacactgat tgcggatgat   840
cgcaacattc acctgttttt tgcaggcgat aatggcagaa tttatagagc aagcatgccg   900
attggcaatt ttccgggaaa ttttggctca agctatacaa caattatgag cgatacaaaa   960
gcgaacctgt ttgaaggcgt tcaagtctat aaagtcaaag gccaaaatca gtacctgatg  1020
attgttgaag caatgggagc gaacggcaga tatttagat catttacagc atcatcactg  1080
tcaggcagct ggacaccgca agcagcaaca gaatcaaatc cgtttgcagg caaagcgaat  1140
tcaggcgcaa catggacaaa tgatatttca catggcgatc tggttcgcga taatccggat  1200
caaacaatga cagttgatcc gtgcaatctg caatttctgt atcaaggcaa agcccgaca  1260 gcaggcggag attataacag actgccgtgg cgtcctggcg ttctgacact gcaaaga     1317
```

```
<210> SEQ ID NO 9
<211> LENGTH: 38
<212> TYPE: DNA
<213> ORGANISM: Artificial sequence
<220> FEATURE:
<223> OTHER INFORMATION: Synthetic construct

<400> SEQUENCE: 9
gttcatcgat cgcatcggct ggcgatacat gcagcctg                                 38

<210> SEQ ID NO 10
<211> LENGTH: 75
<212> TYPE: DNA
<213> ORGANISM: Artificial sequence
<220> FEATURE:
<223> OTHER INFORMATION: Synthetic construct

<400> SEQUENCE: 10 gttttttat tgattaacgc gtttagtgat ggtgatggtg atgtgagcca ccgcctcctc          60
tttgtgtcag cagtc                                                          75
```

US 10,577,594 B2

POLYPEPTIDES HAVING ARABINOFURANOSIDASE ACTIVITY AND POLYNUCLEOTIDES ENCODING SAME

CROSS-REFERENCE TO RELATED APPLICATIONS

This application is a 35 U.S.C. § 371 national application of PCT/US2016/043521 filed Jul. 22, 2016, which claims priority or the benefit under 35 U.S.C. § 119 of U.S. Provisional Application No. 62/196,540 filed Jul. 24, 2015, the contents of which are fully incorporated herein by reference.

STATEMENT AS TO RIGHTS TO INVENTIONS MADE UNDER FEDERALLY SPONSORED RESEARCH AND DEVELOPMENT

This invention was made in part with Government support under Cooperative Agreement DE-EE0006110 awarded by the U.S. Department of Energy. The U.S. government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having arabinofuranosidase activity, catalytic domains, and carbohydrate binding modules, and polynucleotides encoding the polypeptides, catalytic domains, and carbohydrate binding modules. The invention also relates to nucleic acid constructs, vectors, and host cells comprising the polynucleotides as well as methods of producing and using the polypeptides, catalytic domains, and carbohydrate binding modules.

Description of the Related Art

Lignocellulose, the world's largest renewable biomass resource, is composed mainly of lignin, cellulose, and hemicellulose. Cellulose is a polymer of glucose linked by beta-1,4-bonds known as beta-linked glucans. Hemicellulose is composed of xylans, which are polysaccharides formed from 1,4-β-glycoside-linked D-xylopyranoses.

Many microorganisms produce enzymes that hydrolyze the beta-linked glucans and xylans. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Xylanases (e.g., endo-1,4-beta-xylanase, EC 3.2.1.8) hydrolyze internal β-1,4-xylosidic linkages in xylan to produce smaller molecular weight xylose and xylo-oligomers. Beta-xylosidases catalyze the exo-hydrolysis of short beta (1→4)-xylooligosaccharides to remove successive D-xylose residues from non-reducing termini.

The conversion of lignocellulosic feedstocks into ethanol has the advantages of the availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art for new enzymes that can deconstruct cellulosic or hemicellulosic material more efficiently and provide cost-effective enzyme solutions for saccharification of cellulosic material.

The present invention provides polypeptides having arabinofuranosidase activity and polynucleotides thereof and processes of producing and using the polypeptides having arabinofuranosidase activity.

SUMMARY OF THE INVENTION

The present invention relates to isolated polypeptides having arabinofuranosidase activity selected from the group consisting of:

(a) a polypeptide having at least 90% sequence identity to SEQ ID NO: 2 or at least 92% sequence identity to the mature polypeptide of SEQ ID NO: 4;

(b) a polypeptide encoded by a polynucleotide that hybridizes under very high stringency conditions with SEQ ID NO: 1 or the mature polypeptide coding sequence of SEQ ID NO: 3, or the full-length complement thereof;

(c) a polypeptide encoded by a polynucleotide having at least 90% sequence identity to SEQ ID NO: 1 or at least 92% sequence identity to the mature polypeptide coding sequence of SEQ ID NO: 3;

(d) a variant of SEQ ID NO: 2 or the mature polypeptide of SEQ ID NO: 4 comprising a substitution, deletion, and/or insertion at one or more (e.g., several) positions; and (e) a fragment of the polypeptide of (a), (b), (c), or (d) that has arabinofuranosidase activity.

The present invention also relates to isolated polypeptides comprising a catalytic domain selected from the group consisting of:

(a) a catalytic domain having at least 90% sequence identity to amino acids 4 to 303 of SEQ ID NO: 2 or amino acids 173 to 475 of SEQ ID NO: 4;

(b) a catalytic domain encoded by a polynucleotide that hybridizes under very high stringency conditions with nucleotides 10 to 909 of SEQ ID NO: 1 or nucleotides 517 to 1425 of SEQ ID NO: 3, or the full-length complement thereof;

(c) a catalytic domain encoded by a polynucleotide having at least 90% sequence identity to nucleotides 10 to 909 of SEQ ID NO: 1 or at least 92% sequence identity to nucleotides 517 to 1425 of SEQ ID NO: 3;

(d) a variant of amino acids 4 to 303 of SEQ ID NO: 2 or amino acids 173 to 475 of SEQ ID NO: 4 comprising a substitution, deletion, and/or insertion at one or more (e.g., several) positions; and (e) a fragment of the catalytic domain of (a), (b), (c), or (d) that has arabinofuranosidase activity.

The present invention also relates to isolated polypeptides comprising a carbohydrate binding module selected from the group consisting of:

(a) a carbohydrate binding module having at least 92% sequence identity to amino acids 37 to 165 of SEQ ID NO: 4;

(b) a carbohydrate binding module encoded by a polynucleotide that hybridizes under very high stringency conditions with nucleotides 109 to 495 of SEQ ID NO: 3 or the full-length complement thereof;

(c) a carbohydrate binding module encoded by a polynucleotide having at least 92% sequence identity to nucleotides 109 to 495 of SEQ ID NO: 3;

(d) a variant of amino acids 37 to 165 of SEQ ID NO: 4 comprising a substitution, deletion, and/or insertion at one or more (e.g., several) positions; and (e) a fragment of the carbohydrate binding module of (a), (b), (c), or (d) that has binding activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic or hemicellulosic material, comprising: treating the cellulosic or hemicellulosic material with an enzyme composition comprising such a polypeptide having arabinofuranosidase activity.

The present invention also relates to processes for producing a fermentation product, comprising:

(a) saccharifying a cellulosic or hemicellulosic material with an enzyme composition comprising such a polypeptide having arabinofuranosidase activity;

(b) fermenting the saccharified cellulosic or hemicellulosic material with one or more fermenting microorganisms to produce the fermentation product; and (c) recovering the fermentation product from the fermentation.

The present invention also relates to processes of fermenting a cellulosic or hemicellulosic material, comprising: fermenting the cellulosic or hemicellulosic material with one or more (e.g., several) fermenting microorganisms, wherein the cellulosic or hemicellulosic material is saccharified with an enzyme composition and comprising such a polypeptide having arabinofuranosidase activity.

The present invention also relates to an isolated polynucleotide encoding a signal peptide comprising or consisting of amino acids 1 to 36 of SEQ ID NO: 4, which is operably linked to a gene encoding a protein, wherein the gene is foreign to the polynucleotide encoding the signal peptide; nucleic acid constructs, expression vectors, and recombinant host cells comprising the polynucleotides; and methods of producing a protein.

DEFINITIONS

Figure 1:
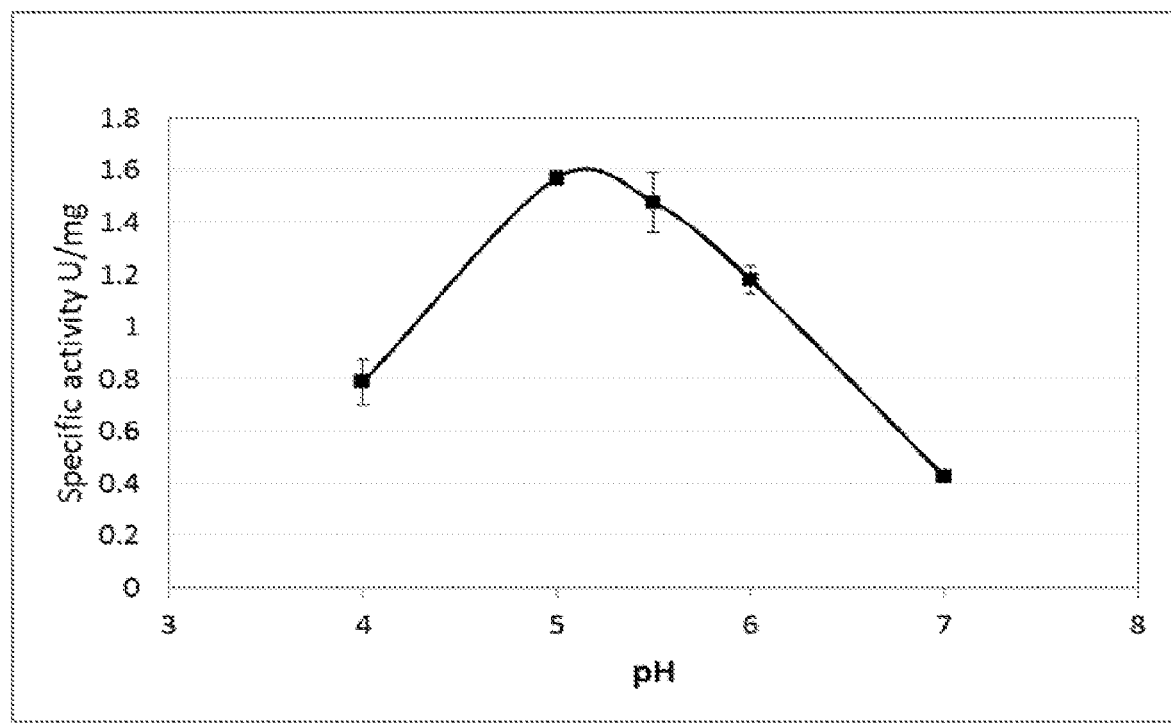
FIG. 1 shows the pH activity profile of an *Actinomadura rubrobrunea* alpha-L-arabinofuranosidase (EbZn184ND) at 50° C.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase or arabinofuranosidase: The term "alpha-L-arabinofuranosidase or arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd.) per ml of 50 mM sodium succinate-NaOH pH 6.2, 75 mM NaCl in a total volume of 200 μL for 30 minutes at 55° C. followed by arabinose analysis by AMINEX® HPX-87H column chromatography (Bio-Rad Laboratories, Inc.). Alpha-L-arabinofuranosidase activity can also be determined according to Example 11.

In one aspect, the polypeptides of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO: 2 or SEQ ID NO: 4.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can be used in the presence of a soluble activating divalent metal cation according to WO 2008/151043 or WO 2012/122518, e.g., manganese or copper.

The AA9 polypeptide can also be used in the presence of a dioxy compound, a bicylic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalase: The term "catalase" means a hydrogen-peroxide:hydrogen-peroxide oxidoreductase (E.C. 1.11.1.6 or E.C. 1.11.1.21) that catalyzes the conversion of two hydrogen peroxides to oxygen and two waters.

Catalase activity can be determined by monitoring the degradation of hydrogen peroxide at 240 nm based on the following reaction:

$$2H_2O_2 \rightarrow 2H_2O + O_2$$

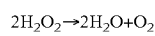

The reaction is conducted in 50 mM phosphate pH 7 at 25° C. with 10.3 mM substrate ($H_2O_2$). Absorbance is monitored spectrophotometrically within 16-24 seconds, which should correspond to an absorbance reduction from 0.45 to 0.4. One catalase activity unit can be expressed as one μmole of $H_2O_2$ degraded per minute at pH 7.0 and 25° C.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the *International Union of Pure and Applied Chemistry* (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, sugar cane straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame that begins with a start codon, such as ATG, GTG, or TTG, and ends with a stop codon, such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Dissolved Oxygen Saturation Level: The saturation level of oxygen is determined at the standard partial pressure (0.21 atmosphere) of oxygen. The saturation level at the standard partial pressure of oxygen is dependent on the temperature and solute concentrations. In an embodiment where the temperature during hydrolysis is 50° C., the saturation level would typically be in the range of 5-5.5 mg oxygen per kg slurry, depending on the solute concentrations. Hence, a concentration of dissolved oxygen of 0.5 to 10% of the saturation level at 50° C. corresponds to an amount of dissolved oxygen in a range from 0.025 ppm (0.5×5/100) to 0.55 ppm (10×5.5/100), such as, e.g., 0.05 to 0.165 ppm, and a concentration of dissolved oxygen of 10-70% of the saturation level at 50° C. corresponds to an amount of dissolved oxygen in a range from 0.50 ppm (10×5/100) to 3.85 ppm (70×5.5/100), such as, e.g., 1 to 2 ppm. In an embodiment, oxygen is added in an amount in the range of 0.5 to 5 ppm, such as 0.5 to 4.5 ppm, 0.5 to 4 ppm, 0.5 to 3.5 ppm, 0.5 to 3 ppm, 0.5 to 2.5 ppm, or 0.5 to 2 ppm.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has arabinofuranosidase. In one aspect, a fragment having arabinofuranosidase activity contains at least 255 amino acid residues, at least 270 amino acid residues, or at least 285 amino acid residues of the mature polypeptide of SEQ ID NO: 2. In another aspect, a fragment having arabinofuranosidase activity contains at least 380 amino acid residues, at least 400 amino acid residues, or at least 420 amino acid residues of the mature polypeptide of SEQ ID NO: 4.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laccase: The term "laccase" means a benzenediol:oxygen oxidoreductase (E.C. 1.10.3.2) that catalyzes the following reaction: 1,2- or 1,4-benzenediol+$O_2$=1,2- or 1,4-benzosemiquinone+2 $H_2O$.

Laccase activity can be determined by the oxidation of syringaldazine (4,4'-[azinobis(methanylylidene)]bis(2,6-dimethoxyphenol)) to the corresponding quinone 4,4'-[azobis(methanylylidene]]bis(2,6-dimethoxycyclohexa-2,5-dien-1-one) by laccase. The reaction (shown below) is detected by an increase in absorbance at 530 nm.

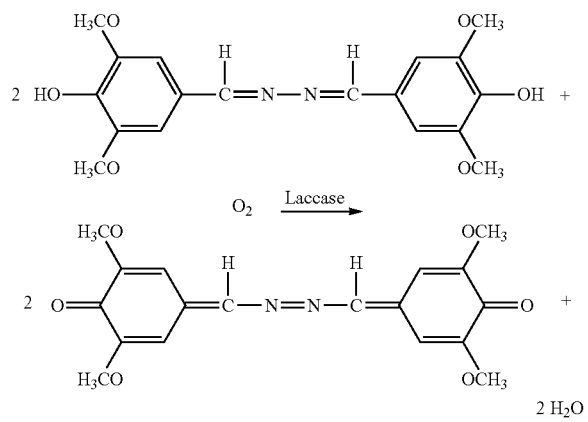

The reaction is conducted in 23 mM MES pH 5.5 at 30° C. with 19 μM substrate (syringaldazine) and 1 g/L polyethylene glycol (PEG) 6000. The sample is placed in a spectrophotometer and the change in absorbance is measured at 530 nm every 15 seconds up to 90 seconds. One laccase unit is the amount of enzyme that catalyzes the conversion of 1 μmole syringaldazine per minute under the specified analytical conditions.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 37 to 475 of SEQ ID NO: 4 based on the SignalP 3.0 program (Bendtsen et al., 2004, *J. Mol. Biol.* 340: 783-795) or SignalP 4.0 program (Petersen et al., 2011, *Nature Methods* 8: 785-786) that predicts amino acids 1 to 36 of SEQ ID NO: 4 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having xylanase activity. In one aspect, the mature polypeptide coding sequence is 109 to 1425 of SEQ ID NO: 3 based on the SignalP 3.0 program (Bendtsen et al., 2004, supra) or SignalP 4.0 program (Petersen et al., 2011, supra) that predicts nucleotides 1 to 108 of SEQ ID NO: 3 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Peroxidase: The term "peroxidase" means an enzyme that converts a peroxide, e.g., hydrogen peroxide, to a less oxidative species, e.g., water. It is understood herein that a peroxidase encompasses a peroxide-decomposing enzyme. The term "peroxide-decomposing enzyme" is defined herein as an donor:peroxide oxidoreductase (E.C. number 1.11.1.x, wherein x=1-3, 5, 7-19, or 21) that catalyzes the reaction reduced substrate (2e$^-$)+ROOR'→oxidized substrate+ROH+R'OH; such as horseradish peroxidase that catalyzes the reaction phenol+$H_2O_2$→quinone+$H_2O$, and catalase that catalyzes the reaction $H_2O_2$+$H_2O_2$→$O_2$+2$H_2O$. In addition to hydrogen peroxide, other peroxides may also be decomposed by these enzymes.

Peroxidase activity can be determined by measuring the oxidation of 2,2'-azino-bis(3-ethylbenzthiazoline-6-sulfonic acid (ABTS) by a peroxidase in the presence of hydrogen peroxide as shown below. The reaction product $ABTS_{ox}$ forms a blue-green color which can be quantified at 418 nm.

The reaction is conducted in 0.1 M phosphate pH 7 at 30° C. with 1.67 mM substrate (ABTS), 1.5 g/L TRITON® X-405, 0.88 mM hydrogen peroxide, and approximately 0.040 units enzyme per ml. The sample is placed in a spectrophotometer and the change in absorbance is measured at 418 nm from 15 seconds up to 60 seconds. One peroxidase unit can be expressed as the amount of enzyme required to catalyze the conversion of 1 μmole of hydrogen peroxide per minute under the specified analytical conditions.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having arabinofuranosidase activity. In one aspect, a subsequence contains at least 765 nucleotides, at least 810 nucleotides, or at least 855 nucleotides of the mature polypeptide coding sequence of SEQ ID NO: 1. In another aspect, a subsequence contains at least 1140 nucleotides, at least 1200 nucleotides, or at least 1260 nucleotides of the mature polypeptide coding sequence of SEQ ID NO: 3.

Variant: The term "variant" means a polypeptide having arabinofuranosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1→4)-linked xylose residues. Xylans of terrestrial plants are heteropolymers possessing a beta-(1→4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc.) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

Polypeptides Having Arabinofuranosidase Activity

In an embodiment, the present invention relates to isolated polypeptides having a sequence identity to the mature polypeptide of SEQ ID NO: 2 of at least 90%, at least 91%, at least 92%, at least 93%, at least 94%, at least 95%, at least 96%, at least 97%, at least 98%, at least 99%, or 100%, or the mature polypeptide of SEQ ID NO: 4 of at least 92%, at least 93%, at least 94%, at least 95%, at least 96%, at least 97%, at least 98%, at least 99%, or 100%, which have arabinofuranosidase activity. In one aspect, the polypeptides differ by up to 10 amino acids, e.g., 1, 2, 3, 4, 5, 6, 7, 8, 9, or 10, from the mature polypeptide of SEQ ID NO: 2 or SEQ ID NO: 4.

A polypeptide of the present invention preferably comprises or consists of the amino acid sequence of SEQ ID NO: 2 or SEQ ID NO: 4 or an allelic variant thereof; or is a fragment thereof having arabinofuranosidase activity. In one aspect, the polypeptide comprises or consists of the mature polypeptide of SEQ ID NO: 2. In another aspect, the polypeptide comprises or consists of the mature polypeptide of SEQ ID NO: 4. In another aspect, the polypeptide comprises or consists of amino acids 25 to 528 of SEQ ID NO: 2. In another aspect, the polypeptide comprises or consists of amino acids 37 to 475 of SEQ ID NO: 4.

In another embodiment, the present invention relates to isolated polypeptides having arabinofuranosidase activity encoded by polynucleotides that hybridize under very low stringency conditions, low stringency conditions, medium stringency conditions, medium-high stringency conditions, high stringency conditions, or very high stringency conditions with SEQ ID NO: 1 or the mature polypeptide coding sequence of SEQ ID NO: 3 or the full-length complement thereof (Sambrook et al., 1989, *Molecular Cloning, A Laboratory Manual*, 2d edition, Cold Spring Harbor, N.Y.).

The polynucleotide of SEQ ID NO: 1 or SEQ ID NO: 3, or a subsequence thereof, as well as the polypeptide of SEQ ID NO: 2 or SEQ ID NO: 4, or a fragment thereof, may be used to design nucleic acid probes to identify and clone DNA encoding polypeptides having arabinofuranosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having arabinofuranosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or SEQ ID NO: 3, or a subsequence thereof, the carrier material is used in a Southern blot.

For purposes of the present invention, hybridization indicates that the polynucleotides hybridize to a labeled nucleic acid probe corresponding to (i) SEQ ID NO: 1 or SEQ ID NO: 3; (ii) SEQ ID NO: 1 or the mature polypeptide coding sequence of SEQ ID NO: 3; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is SEQ ID NO: 1 or nucleotides 109 to 1425 of SEQ ID NO: 3, or a subsequence thereof. In another aspect, the nucleic acid probe is a polynucleotide that encodes the polypeptide of SEQ ID NO: 2 or SEQ ID NO: 4; the mature polypeptide of SEQ ID NO: 4; or a fragment thereof. In another aspect, the nucleic acid probe is SEQ ID NO: 1 or SEQ ID NO: 3.

In another embodiment, the present invention relates to isolated polypeptides having arabinofuranosidase activity encoded by polynucleotides having a sequence identity to the mature polypeptide coding sequence of SEQ ID NO: 1 of at least 90%, e.g., at least 91%, at least 92%, at least 93%, at least 94%, at least 95%, at least 96%, at least 97%, at least 98%, at least 99%, or 100%, or the mature polypeptide coding sequence of SEQ ID NO: 3 of at least 92%, e.g., at least 93%, at least 94%, at least 95%, at least 96%, at least 97%, at least 98%, at least 99%, or 100%.

In another embodiment, the present invention relates to variants of the mature polypeptide of SEQ ID NO: 2 or SEQ ID NO: 4 comprising a substitution, deletion, and/or insertion at one or more (e.g., several) positions. In one aspect, the number of amino acid substitutions, deletions and/or insertions introduced into the mature polypeptide of SEQ ID NO: 2 or SEQ ID NO: 4 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for arabinofuranosidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Arabinofuranosidase Activity

A polypeptide having arabinofuranosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is an *Actinomadura* polypeptide. In another aspect, the polypeptide is an *Actinomadura alba, Actinomadura apis, Actinomadura atramentaria, Actinomadura bangladeshensis, Actinomadura catellatispora, Actinomadura citrea, Actinomadura coerulea, Actinomadura coeruleoviolacea, Actinomadura cremea, Actinomadura dassonvillei, Actinomadura ferruginea, Actinomadura fibrosa, Actinomadura flavalba, Actinomadura formosensis, Actinomadura fulvescens, Actinomadura geliboluensis, Actinomadura glauciflava Actinomadura helvata, Actinomadura keratinilytica, Actinomadura kijaniata, Actinomadura libanotica, Actinomadura livida, Actinomadura luteofluorescens, Actinomadura madurae, Actinomadura malachitica, Actinomadura nitritigenes, Actinomadura pelletieri, Actinomadura pusilla, Actinomadura roseola, Actinomadura roseoviolacea, Actinomadura rubra, Actinoma-* dura rubrobrunea, Actinomadura salmonea, Actinomadura spadix, Actinomadura spiralis, or Actinomadura verrucosospora polypeptide.

In another aspect, the polypeptide is an *Actinomadura alba* polypeptide. In another aspect, the polypeptide is an *Actinomadura apis* polypeptide. In another aspect, the polypeptide is an *Actinomadura atramentaria* polypeptide. In another aspect, the polypeptide is an *Actinomadura bangladeshensis* polypeptide. In another aspect, the polypeptide is an *Actinomadura catellatispora* polypeptide. In another aspect, the polypeptide is an *Actinomadura citrea* polypeptide. In another aspect, the polypeptide is an *Actinomadura coerulea* polypeptide. In another aspect, the polypeptide is an *Actinomadura coeruleoviolacea* polypeptide. In another aspect, the polypeptide is an *Actinomadura cremea* polypeptide. In another aspect, the polypeptide is an *Actinomadura dassonvillei* polypeptide. In another aspect, the polypeptide is an *Actinomadura ferruginea* polypeptide. In another aspect, the polypeptide is an *Actinomadura fibrosa* polypeptide. In another aspect, the polypeptide is an *Actinomadura flavalba* polypeptide. In another aspect, the polypeptide is an *Actinomadura formosensis* polypeptide. In another aspect, the polypeptide is an *Actinomadura fulvescens* polypeptide. In another aspect, the polypeptide is an *Actinomadura geliboluensis* polypeptide. In another aspect, the polypeptide is an *Actinomadura glauciflava* polypeptide. In another aspect, the polypeptide is an *Actinomadura helvata* polypeptide. In another aspect, the polypeptide is an *Actinomadura keratinilytica* polypeptide. In another aspect, the polypeptide is an *Actinomadura kijaniata* polypeptide. In another aspect, the polypeptide is an *Actinomadura libanotica* polypeptide. In another aspect, the polypeptide is an *Actinomadura livida* polypeptide. In another aspect, the polypeptide is an *Actinomadura luteofluorescens* polypeptide. In another aspect, the polypeptide is an *Actinomadura madurae* polypeptide. In another aspect, the polypeptide is an *Actinomadura malachitica* polypeptide. In another aspect, the polypeptide is an *Actinomadura nitritigenes* polypeptide. In another aspect, the polypeptide is an *Actinomadura pelletieri* polypeptide. In another aspect, the polypeptide is an *Actinomadura pusilla* polypeptide. In another aspect, the polypeptide is an *Actinomadura roseola* polypeptide. In another aspect, the polypeptide is an *Actinomadura roseoviolacea* polypeptide. In another aspect, the polypeptide is an *Actinomadura rubra* polypeptide. In another aspect, the polypeptide is an *Actinomadura rubrobrunea* polypeptide, e.g., a polypeptide obtained from *Actinomadura rubrobrunea* DSM 43750. In another aspect, the polypeptide is an *Actinomadura salmonea* polypeptide. In another aspect, the polypeptide is an *Actinomadura spadix* polypeptide. In another aspect, the polypeptide is an *Actinomadura spiralis* polypeptide. In another aspect, the polypeptide is an *Actinomadura verrucosospora* polypeptide.

In another aspect, the polypeptide is a *Streptomyces* polypeptide. In another aspect, the polypeptide is a *Streptomyces mexicanus, Streptomyces thermoalcalitolerans, Streptomyces thermocoprophilus, Streptomyces spectabilis, Streptomyces thermogriseus, Streptomyces thermonitrificans*, or *Streptomyces thermovulgaris* polypeptide.

In another aspect, the polypeptide is a *Streptomyces mexicanus* polypeptide. In another aspect, the polypeptide is a *Streptomyces thermoalcalitolerans* polypeptide, e.g., a *Streptomyces thermoalcalitolerans* DSM 41741 polypeptide. In another aspect, the polypeptide is a *Streptomyces thermocoprophilus* polypeptide. In another aspect, the polypeptide is a *Streptomyces spectabilis* polypeptide. In another aspect, the polypeptide is a *Streptomyces thermogriseus* polypeptide. In another aspect, the polypeptide is a *Streptomyces thermonitrificans* polypeptide. In another aspect, the polypeptide is a *Streptomyces thermovulgaris* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 4 to 303 of SEQ ID NO: 2 of at least 90%, e.g., at least 91%, at least 92%, at least 93%, at least 94%, at least 95%, at least 96%, at least 97%, at least 98%, at least 99%, or 100%, or amino acids 173 to 475 of SEQ ID NO: 4 of at least 92%, e.g., at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 4 to 303 of SEQ ID NO: 2 or amino acids 173 to 475 of SEQ ID NO: 4.

The catalytic domain preferably comprises or consists of amino acids 4 to 303 of SEQ ID NO: 2 or amino acids 173 to 475 of SEQ ID NO: 4, or an allelic variant thereof; or is a fragment thereof having arabinofuranosidase activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with nucleotides 10 to 909 of SEQ ID NO: 1 or nucleotides 517 to 1425 of SEQ ID NO: 3, or the full-length complement thereof (Sambrook et al., 1989, supra).

In another embodiment, the present invention also relates to catalytic domains encoded by polynucleotides having a sequence identity to nucleotides 10 to 909 of SEQ ID NO: 1 of at least 90%, e.g., at least 91%, at least 92%, at least 93%, at least 94%, at least 95%, at least 96%, at least 97%, at least 98%, at least 99%, or 100%, or nucleotides 517 to 1425 of SEQ ID NO: 3 of at least 92%, e.g., at least 93%, at least 94%, at least 95%, at least 96%, at least 97%, at least 98%, at least 99%, or 100%.

The polynucleotide encoding the catalytic domain preferably comprises or consists of nucleotides 10 to 909 of SEQ ID NO: 1 or nucleotides 517 to 1425 of SEQ ID NO: 3.

In another embodiment, the present invention also relates to catalytic domain variants of amino acids 4 to 303 of SEQ ID NO: 2 or amino acids 173 to 475 of SEQ ID NO: 4 comprising a substitution, deletion, and/or insertion at one or more (e.g., several) positions. In one aspect, the number of amino acid substitutions, deletions and/or insertions introduced into the sequence of amino acids 4 to 303 of SEQ ID NO: 2 or amino acids 173 to 475 of SEQ ID NO: 4 is up to 10, e.g., 1, 2, 3, 4, 5, 6, 8, 9, or 10.

In another aspect, a polypeptide comprising a catalytic domain of the present invention may further comprise a carbohydrate binding module.

Carbohydrate Binding Modules

In one embodiment, the present invention also relates to carbohydrate binding modules having a sequence identity to amino acids 37 to 165 of SEQ ID NO: 4 of at least 92%, e.g., at least 93%, at least 94%, at least 95%, at least 96%, at least 97%, at least 98%, at least 99%, or 100%. In one aspect, the carbohydrate binding modules comprise amino acid sequences that differ by up to 10 amino acids, e.g., 1, 2, 3, 4, 5, 6, 7, 8, 9, or 10, from amino acids 37 to 165 of SEQ ID NO: 4.

The carbohydrate binding module preferably comprises or consists of amino acids 37 to 165 of SEQ ID NO: 4, or an allelic variant thereof; or is a fragment thereof having carbohydrate binding activity.

In another embodiment, the present invention also relates to carbohydrate binding modules encoded by polynucleotides that hybridize under very low stringency conditions, low stringency conditions, medium stringency conditions, medium-high stringency conditions, high stringency conditions, or very high stringency conditions (as defined above) with nucleotides 109 to 495 of SEQ ID NO: 3, or the full-length complement thereof (Sambrook et al., 1989, supra).

In another embodiment, the present invention also relates to carbohydrate binding modules encoded by polynucleotides having a sequence identity to nucleotides 109 to 495 of SEQ ID NO: 3 of at least 92%, e.g., at least 93%, at least 94%, at least 95%, at least 96%, at least 97%, at least 98%, at least 99%, or 100%.

The polynucleotide encoding the carbohydrate binding module preferably comprises or consists of nucleotides 109 to 495 of SEQ ID NO: 3.

In another embodiment, the present invention also relates to carbohydrate binding module variants of amino acids 37 to 165 of SEQ ID NO: 4 comprising a substitution, deletion, and/or insertion at one or more (e.g., several) positions. In one aspect, the number of amino acid substitutions, deletions and/or insertions introduced into the sequence of amino acids 37 to 165 of SEQ ID NO: 4 is up to 10, e.g., 1, 2, 3, 4, 5, 6, 8, 9, or 10.

A catalytic domain operably linked to the carbohydrate binding module may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding a polypeptide, a catalytic domain, or carbohydrate binding module of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Actinomadura* or *Streptomyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as SEQ ID NO: 1 or the mature polypeptide coding sequence of SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coil* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a wild-type cell under conditions conducive for production of the polypeptide; and optionally, (b) recovering the polypeptide. In one aspect, the cell is an *Actinomadura* cell. In another aspect, the cell is an *Actinomadura rubrobrunea* cell. In another aspect, the cell is *Actinomadura rubrobrunea* DSM 43750. In another aspect, the cell is a *Streptomyces* cell. In another aspect, the cell is a *Streptomyces thermoalcalitolerans* cell. In another aspect, the cell is *Streptomyces thermoalcalitolerans* DSM 41741.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed (Sticklen, 2008, *Nature Reviews* 9: 433-443). For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an AA9 polypeptide, a cellulose inducible protein (CIP), a catalase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the arabinofuranosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide, a cellulose inducible protein (CIP), a catalase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of uses of the compositions of the present invention. The dosage of the composition and other conditions under which the composition is used may be determined on the basis of methods known in the art.

Uses

The present invention is also directed to the following processes for using the polypeptides having arabinofuranosidase activity, or compositions thereof.

The present invention also relates to processes for degrading a cellulosic or hemicellulosic material, comprising: treating the cellulosic or hemicellulosic material with an enzyme composition comprising a polypeptide having arabinofuranosidase activity of the present invention. In one aspect, the processes further comprise recovering the degraded cellulosic or hemicellulosic material. Soluble products from the degradation of the cellulosic or hemicellulosic material can be separated from insoluble cellulosic or hemicellulosic material using methods known in the art such as, for example, centrifugation, filtration, or gravity settling.

The present invention also relates to processes of producing a fermentation product, comprising: (a) saccharifying a cellulosic or hemicellulosic material with an enzyme composition comprising a polypeptide having arabinofuranosidase activity of the present invention; (b) fermenting the saccharified cellulosic or hemicellulosic material with one or more (e.g., several) fermenting microorganisms to produce the fermentation product; and (c) recovering the fermentation product from the fermentation.

The present invention also relates to processes of fermenting a cellulosic or hemicellulosic material, comprising: fermenting the cellulosic or hemicellulosic material with one or more (e.g., several) fermenting microorganisms, wherein the cellulosic or hemicellulosic material is saccharified with an enzyme composition comprising a polypeptide having arabinofuranosidase activity of the present invention. In one aspect, the fermenting of the cellulosic or hemicellulosic material produces a fermentation product. In another aspect, the processes further comprise recovering the fermentation product from the fermentation.

The processes of the present invention can be used to saccharify the cellulosic or hemicellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic or hemicellulosic material typically involves pretreatment, enzymatic hydrolysis (saccharification), and fermentation.

The processing of the cellulosic or hemicellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic or hemicellulosic material to fermentable sugars, e.g., glucose, cellobiose, and pentose monomers, and then ferment the fermentable sugars to ethanol. In SSF, the enzymatic hydrolysis of the cellulosic or hemicellulosic material and the fermentation of sugars to ethanol are combined in one step (Philippidis, G. P., 1996, Cellulose bioconversion technology, in *Handbook on Bioethanol: Pro-* duction and Utilization, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic or hemicellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic or hemicellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic or hemicellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or hemicellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or hemicellulosic material is heated to disrupt the plant cell wall components, including lignin, hemicellulose, and cellulose to make the cellulose and other fractions, e.g., hemicellulose, accessible to enzymes. The cellulosic or hemicellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic or hemicellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or hemicellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/

110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic or hemicellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic or hemicellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic or hemicellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or hemicellulosic material is present during pretreatment in amounts preferably between 10-80 wt. %, e.g., 20-70 wt. % or 30-60 wt. %, such as around 40 wt. %. The pretreated cellulosic or hemicellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or hemicellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or hemicellulosic material is subjected to physical (mechanical) or chemical pretreatment, or any combination thereof, to promote the separation and/or release of cellulose, hemicellulose, and/or lignin.

Biological Pretreatment. The term "biological pretreatment" refers to any biological pretreatment that promotes the separation and/or release of cellulose, hemicellulose, and/or lignin from the cellulosic or hemicellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic or hemicellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by one or more enzyme compositions in one or more stages. The hydrolysis can be carried out as a batch process or series of batch processes. The hydrolysis can be carried out as a fed batch or continuous process, or series of fed batch or continuous processes, where the cellulosic or hemicellulosic material is fed gradually to, for example, a hydrolysis solution containing an enzyme composition. In an embodiment the saccharification is a continuous saccharification in which a cellulosic material and a cellulolytic enzyme composition are added at different intervals throughout the saccharification and the hydrolysate is removed at different intervals throughout the saccharification. The removal of the hydrolysate may occur prior to, simultaneously with, or after the addition of the cellulosic material and the cellulolytic enzyme composition.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s).

The saccharification is generally performed in stirred-tank reactors or fermentors under controlled pH, temperature, and mixing conditions. Suitable process time, temperature and pH conditions can readily be determined by one skilled in the art. For example, the total saccharification time can last up to 200 hours, but is typically performed for preferably about 4 to about 120 hours, e.g., about 12 to about 96 hours or about 24 to about 72 hours. The temperature is in the range of preferably about 25° C. to about 80° C., e.g., about 30° C. to about 70° C., about 40° C. to about 60° C., or about 50° C. to about 55° C. The pH is in the range of preferably about 3 to about 9, e.g., about 3.5 to about 8, about 4 to about 7, about 4.2 to about 6, or about 4.3 to about 5.5.

The dry solids content is in the range of preferably about 5 to about 50 wt. %, e.g., about 10 to about 40 wt. % or about 20 to about 30 wt. %.

In one aspect, the saccharification is performed in the presence of dissolved oxygen at a concentration of at least 0.5% of the saturation level.

In an embodiment of the invention the dissolved oxygen concentration during saccharification is in the range of at least 0.5% up to 30% of the saturation level, such as at least 1% up to 25%, at least 1% up to 20%, at least 1% up to 15%, at least 1% up to 10%, at least 1% up to 5%, and at least 1% up to 3%. In a preferred embodiment, the dissolved oxygen concentration is maintained at a concentration of at least 0.5% up to 30% of the saturation level, such as at least 1% up to 25%, at least 1% up to 20%, at least 1% up to 15%, at least 1% up to 10%, at least 1% up to 5%, and at least 1% up to 3% during at least 25%, such as at least 50% or at least 75% of the saccharification period. When the enzyme composition comprises an oxidoreductase the dissolved oxygen concentration may be higher up to 70% of the saturation level.

Oxygen is added to the vessel in order to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, MO, USA.

The enzyme compositions can comprise any protein useful in degrading the cellulosic or hemicellulosic material.

In one aspect, the enzyme composition comprises or further comprises one or more (e.g., several) proteins selected from the group consisting of a cellulase, an AA9 polypeptide, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an AA9 polypeptide. In another aspect, the enzyme composition comprises an endoglucanase and an AA9 polypeptide. In another aspect, the enzyme composition comprises a cellobiohydrolase and an AA9 polypeptide. In another aspect, the enzyme composition comprises a beta-glucosidase and an AA9 polypeptide. In another aspect, the enzyme composition comprises an endoglucanase and a cellobiohydrolase. In another aspect, the enzyme composition comprises an endoglucanase I, an endoglucanase II, or a combination of an endoglucanase I and an endoglucanase II, and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises an endoglucanase I, an endoglucanase II, or a combination of an endoglucanase I and an endoglucanase II, and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, an AA9 polypeptide, and a cellobiohydrolase. In another aspect, the enzyme composition comprises an endoglucanase I, an endoglucanase II, or a combination of an endoglucanase I and an endoglucanase II, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and an AA9 polypeptide. In another aspect, the enzyme composition comprises a beta-glucosidase, an AA9 polypeptide, and a cellobiohydrolase. In another aspect, the enzyme composition comprises a beta-glucosidase, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase I, an endoglucanase II, or a combination of an endoglucanase I and an endoglucanase II, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and an AA9 polypeptide. In another aspect, the enzyme composition comprises an endoglucanase I, an endoglucanase II, or a combination of an endoglucanase I and an endoglucanase II, a beta-glucosidase, an AA9 polypeptide, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the enzyme composition comprises a pectinase. In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having arabinofuranosidase activity depend on several factors including, but not limited to, the mixture of cellulolytic enzymes and/or hemicellulolytic enzymes, the cellulosic or hemicellulosic material, the concentration of cellulosic or hemicellulosic material, the pretreatment(s) of the cellulosic or hemicellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic or hemicellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic or hemicellulosic material.

In another aspect, an effective amount of a polypeptide having arabinofuranosidase activity to the cellulosic or hemicellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or hemicellulosic material.

In another aspect, an effective amount of a polypeptide having arabinofuranosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or hemicellulosic material, e.g., AA9 polypeptides can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 2005/093050), *Erwinia carotovara* endoglucanase (Saarilahti et al., 1990, *Gene* 90: 9-14), *Thermobifida fusca* endoglucanase III (WO 2005/093050), and *Thermobifida fusca* endoglucanase V (WO 2005/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830), *Trichoderma reesei* strain No. VTT-D-80133 endoglucanase (GenBank: M15665), and *Penicillium pinophilum* endoglucanase (WO 2012/062220).

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

In the processes of the present invention, any AA9 polypeptide can be used as a component of the enzyme composition.

Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (emersoni0 (WO 2011/041397 and WO 2012/000892), *Thermoascus crustaceous* (WO 2011/041504), *Aspergillus aculeatus* (WO 2012/125925), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206), and *Talaromyces thermophilus* (WO 2012/129697 and WO 2012/130950).

In one aspect, the AA9 polypeptide is used in the presence of a soluble activating divalent metal cation according to WO 2008/151043 or WO 2012/122518, e.g., manganese or copper.

In another aspect, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{1}$, about $10^{-4}$ to about $10^{1}$, about $10^{-3}$ to about $10^{-1}$, or about $10^{-3}$ to about $10^{2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL: Q92458), *Talaromyces emersonii* (SwissProt:Q8X212), and *Talaromyces thermophilus* (GeneSeqP:BAA22816).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:QOCJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus lentilus* catalase, *Aspergillus fumigatus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic or hemicellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or hemicellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic or hemicellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, G. P., 1996, Cellulose bioconversion technology, in *Handbook on Bioethanol: Production and Utilization*, Wyman, C. E., ed., Taylor & Francis, Washington, D.C., 179-212).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIO-FERM® AFT and XR (Lallemand Specialties, Inc., USA), ETHANOL RED® yeast (Lesaffre et Co, pagnie, France), FALI® (AB Mauri Food Inc., USA), FERMIOL® (Rymco International AG, Denmark), GERT STRAND™ (Gert Strand AB, Sweden), and SUPERSTART™ and THERMOSACC® fresh yeast (Lallemand Specialties, Inc., USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises a polynucleotide encoding a polypeptide having arabinofuranosidase activity of the present invention.

In another aspect, the fermenting organism comprises one or more polynucleotides encoding one or more cellulolytic enzymes, hemicellulolytic enzymes, and accessory enzymes described herein.

It is well known in the art that the organisms described above can also be used to produce other substances, as described herein.

The fermenting microorganism is typically added to the degraded cellulosic or hemicellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or hemicellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or hemicellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 36 of SEQ ID NO: 4. The polynucleotides may further comprise a gene encoding a protein, which is operably linked to the signal peptide. The protein is preferably foreign to the signal peptide. In one aspect, the polynucleotide encoding the signal peptide is nucleotides 1 to 108 of SEQ ID NO: 3.

The present invention also relates to nucleic acid constructs, expression vectors and recombinant host cells comprising such a polynucleotide.

The present invention also relates to methods of producing a protein, comprising (a) cultivating a recombinant host cell comprising such a polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Media

FNL medium was composed of 55 g of BD Difco™ Lactobacilli MRS broth, 50 mM MOPS, 10 ml of 1 M CaCl$_2$ and deionized water to 1 liter; pH to 6.5.

LB medium was composed of 10 g of tryptone, 5 g of yeast extract, and 5 g of NaCl LB+Amp medium was composed of 10 g of tryptone, 5 g of yeast extract, 5 g of NaCl, and 1 ml of 100 mg/ml ampicillin stock solution.

LB+Amp plates were composed of 10 g of tryptone, 5 g of yeast extract, 5 g of NaCl, 15 g of Bacto agar, and 1 ml of 100 mg/ml ampicillin stock solution, and deionized water to 1 liter.

Opt-MRS medium was composed of 55 g of BD Difco™ Lactobacilli MRS broth, 125 mM MOPS, 10 ml of 1 M CaCl$_2$, and deionized water to 1 liter.

TBAB+CM plates were composed of 33 g of Tryptose blood agar base, 0.5 ml of 10 mg/ml chloramphenicol stock solution, and deionized water to 1 liter.

2×YT+Amp plates were composed of 16 g of tryptone, 10 g of yeast extract, 5 g of NaCl, 15 g of Bacto agar, and 1 ml of 100 mg/ml ampicillin stock solution, and deionized water to 1 liter.

Example 1: Generation of *Bacillus subtilis* Host Strain IH14

*Bacillus subtilis* strain IH14 is essentially *B. subtilis* strain SMO25 (U.S. Pat. No. 8,580,536) with the following modifications: (1) The endogenous xynA gene encoding a GH11 xylanase was deleted; (2) a spectinomycin resistance marker from transposon Tn554 (Murphy et al., 1985, *EMBO Journal* 4(12): 3357-3365) and a $P_{amyL4199}/P_{short\ consensus\ amyQ}/P_{cryIIIA}$ triple tandem promoter (U.S. Pat. No. 8,268,586) were inserted at the pel locus (thereby deleting the pelB gene which encodes pectate lyase); and (3) a neomycin resistance marker from plasmid pUB110 (McKenzie et al., 1986, *Plasmid* 15(2): 93-103) and a $P_{amyL4199}/P_{short\ consensus\ amyQ}/P_{cryIIIA}$ triple tandem promoter driving transcription of an extra copy of the *B. subtilis* prsA gene (encodes a chaperone to facilitate protein folding) has been inserted into the bglC locus (thereby deleting the bglC gene which encodes a GH5 endoglucanase).

Example 2: Construction of Plasmid pTH295

Plasmid pTH153 (US 2013/0014293), an expression vector containing a *Thermobifida fusca* xylanase gene, was gapped by digestion with Sac I and Mlu I. The digestion was verified by fractionating an aliquot of the digestion by 0.8% agarose gel electrophoresis in 40 mM Tris base, 20 mM sodium acetate, 1 mM disodium EDTA (TAE) buffer where expected fragments of 7046 bp (gapped) and 691 bp (*Thermobifida fusca* GH10 xylanase) were obtained. The 7046 bp (gapped) fragment was excised from the gel and purified using a QIAQUICK® Gel Extraction Kit (QIAGEN). In-Fusion® HD Cloning (Clontech Laboratories, Inc.) was performed following the manufacturer's directions using a 555 bp synthetic DNA fragment synthesized by GeneArt® (Life Technologies, Thermo Fisher Scientific) which consisted of the *Bacillus clausii* alkaline serine protease gene ribosomal binding site, the *B. clausii* alkaline serine protease signal sequence, a multiple cloning site, and a dockerin gene from *Clostridium cellulovorans* EngE (GenBank Accession number: AAD39739.1 according to You et al., 2012, *Angewandte Chemie International Edition* 51(35): 8787-8790) The 555 bp synthetic DNA fragment also contained a 30 bp overhang at the 5' end consisting of overlapping bases identical to the 3' end of the cryIIIA stabilizer on plasmid pTH153 as well as a Sac I site upstream of the *B. clausii* alkaline serine protease gene ribosomal binding site. Additionally, the 555 bp synthetic DNA fragment contained a 30 bp overhang at the 3' end consisting of overlapping nucleotide bases identical to the 5' end of the *B. clausii* alkaline serine protease gene transcriptional terminator as well as an Mlu I site downstream of the *C. cellulovorans* EngE dockerin gene. A total of 50 ng of the 555 bp synthetic DNA fragment and 200 ng of plasmid pTH153 (digested with Sac I and Mlu I) were used in a reaction composed of 2 µl of 5× In-Fusion® HD enzyme mixture in a final volume of 10 µl. The reaction was incubated for 15 minutes at 50° C. and then placed on ice. To transform *E. coli* XL10-GOLD® Ultra-competent Cells (Stratagene), 3 µl of the reaction were used according to manufacturer's instructions. Transformants were selected on LB+Amp plates. Plasmid DNA from several of the resulting *E. coli* transformants was prepared using a BIOROBOT® 9600 (QIAGEN).

One plasmid designated pTH295 comprising the *B. clausii* alkaline serine protease gene ribosomal binding site, the *B. clausii* alkaline serine protease signal sequence, the multiple cloning site, and the *C. cellulovorans* EngE dockerin gene was identified and the full-length polynucleotide sequence was determined using a 3130xl Genetic Analyzer (Applied Biosystems).

Example 3: Isolation of *Actinomadura rubrobrunea* and Genome Sequencing

A strain of the species *Actinomadura rubrobrunea* was isolated from Danish soil on Casitone-Yeast Extract based medium (BD Difco™) at 55° C., pH 7. Taxonomic positioning of the strain was performed by 16S rDNA sequence comparison. The type strain of this species can be purchased from the Leibniz-Institute DSMZ-Deutsche Sammlung von Mikroorganismen und Zellkulturen GmbH deposition number DSM 43750. A genomic DNA preparation of the isolated strain was subjected to genome sequencing (Fasteris SA, Switzerland) and genes encoding glycoside hydrolases were identified by bioinformatic genome annotation. Genes specifically encoding alpha-L-arabinofuranosidases of glycoside hydrolase Family 62 were identified by BLAST similarity searching.

Example 4: Characterization of Genomic DNA from *Actinomadura rubrobrunea* Encoding a GH62 Alpha-L-Arabinofuranosidase The genomic DNA sequence and deduced amino acid sequence of a partial GH62 alpha-L-arabinofuranosidase coding sequence from *Actinomadura rubrobrunea* are shown in SEQ ID NO: 1 and SEQ ID NO: 2, respectively. The partial coding sequence is 912 bp including the stop codon. Using the SignalP 4.0 program (Petersen et al., 2011, *Nature Methods* 8: 785-786), no signal peptide was predicted, however, the amino terminus of the encoded polypeptide appears to be missing. The predicted partial protein contains 303 amino acids with a predicted molecular mass of 33.2 kDa and a predicted isoelectric point of 5.6. Although the polypeptide is truncated at the amino terminus, the predicted GH62 catalytic domain is intact and extends from approximately amino acid 4 to 303 of the polypeptide.

A comparative pairwise global alignment of amino acid sequences was determined using the Needleman and Wunsch algorithm (Needleman and Wunsch, 1970, *J. Mol. Biol.* 48: 443-453) with a gap open penalty of 10, a gap extension penalty of 0.5, and the EBLOSUM62 matrix. The alignment showed that the deduced amino acid sequence of the *Actinomadura rubrobrunea* genomic DNA encoding a GH62 alpha-L-arabinofuranosidase shares 89.4% identity (excluding gaps) to the deduced amino acid sequence of a GH62 alpha-L-arabinofuranosidase from *Streptomyces griseoflavus* (UNIPROT:D9YOM4).

Example 5: Construction of Plasmid pEbZn184ND

A synthetic gene coding for the mature polypeptide of the *Actinomadura rubrobrunea* GH62 alpha-L-arabinofuranosidase of SEQ ID NO: 2 was optimized for expression in *Bacillus subtilis* using GeneArt® GeneOptimzer® software (Thermo Fisher Scientific) and synthesized by Life Technologies. The optimized sequence is shown in SEQ ID NO: 5. The synthetic DNA was subcloned into plasmid pTH295. This was accomplished by digesting pTH295 with Kpn I and Mlu I to remove the multiple cloning site and the *C. cellulovorans* EngE dockerin gene. The synthetic DNA was amplified by PCR using the primers shown below designed to amplify the gene and add regions of identity to the pTH295 vector and a His-6 tag downstream of the synthetic gene coding sequence.

```
Forward primer:
                                            (SEQ ID NO: 6)
5'-GTTGCTTTTAGTTCATCGATCGCATCGGCTCCGACATGCGATC
TGC-3'

Reverse primer:
                                            (SEQ ID NO: 7)
5'-GTTTTTTTATTGATTAACGCGTTTAGTGATGGTGATGGTGATG
TGAGCCACCGCCTCCTCTTTGTGTCAGCAGTC-3'
```

A total of 50 picomoles of each of the primers above were used in an amplification reaction containing 100 ng of synthetic DNA, 1×HF Buffer (Thermo Fisher Scientific), 2 µl of a blend of dATP, dTTP, dGTP, and dCTP, each at 10 mM, and 1 µl of Phusion polymerase (Thermo Fisher Scientific) in a final volume of 100 µl. The amplification reaction was performed in a thermocycler programmed for 1 cycle at 98° C. for 30 seconds; and 30 cycles each at 98° C. for 5 seconds, 62° C. for 30 seconds, and 72° C. for 30 seconds. After the 30 cycles, the reaction was heated for 10 minutes at 72° C. The heat block then went to a 12° C. soak cycle. The PCR product was isolated by 1.0% agarose gel electrophoresis using TAE buffer where a 906 bp band was excised from the gel and extracted using an Agarose Gel Purification Kit (Clontech Laboratories, Inc.) according to the manufacturer's instructions.

The homologous ends of the PCR product and plasmid pTH295, digested with Kpn I and Mlu I, were joined using an IN-FUSION™ Advantage PCR Cloning Kit (Clontech Laboratories, Inc.). A total of 78 ng of the PCR product and 183 ng of plasmid pTH295 (digested with Kpn I and Mlu I) were used in a reaction containing 2 µl of 5× IN-FUSION™ reaction buffer (Clontech Laboratories, Inc.) and 1 µl of IN-FUSION™ enzyme (Clontech Laboratories, Inc.) in a final volume of 10 µl. The reaction was incubated for 15 minutes at 37° C., followed by 15 minutes at 50° C., and then placed on ice. A 2.5 µl volume of the reaction was used to transform *E. coli* STELLAR® Cells (Stratagene) according to the manufacturer's instructions. Transformants were selected on 2×YT+Amp plates after overnight growth at 37° C. and the selected transformants were grown overnight in 3 ml of LB+Amp medium at 37° C. Plasmid DNA from several of the resulting *E. coli* transformants was prepared using a BIOROBOT® 9600. Verification of insertion of the PCR product into the vector was confirmed by digesting with Sac I and Not I. A plasmid showing the correct insert was designated pEbZn184ND.

Example 6: Expression of the *Actinomadura rubrobrunea* GH62 Alpha-L-Arabinofuranosidase Plasmid pEbZn184ND was transformed into *Bacillus subtilis* strain IH14 as follows. One µg of plasmid pEbZn184ND was linearized with Sal I. Competent cells of *B. subtilis* IH14 were prepared according to Anagnostopoulos and Spizizen, 1961, *Journal of Bacteriology* 81: 741-746. Cells were then centrifuged at 3836×g for 10 minutes. Eighteen ml of cell supernatant were added to 2 ml of glycerol. The cell pellet was resuspended in the supernatant/glycerol mixture, distributed in 0.5 ml aliquots, and frozen for storage at −80° C.

A 0.5 ml volume of Spizizen II medium with 2 mM EGTA was added to 0.5 ml of the frozen competent *B. subtilis* IH14 cells. The cells were thawed in a water bath at 37° C. and divided into 18 tubes (approximately 50 µl each). One µg of linearized plasmid DNA was added to an aliquot of the competent cells and induced with 0.5 ml of chloramphenicol at a final concentration of 0.2 µg per ml. Transformation reactions were incubated at 37° C. for 1 hour with shaking at 250 rpm. Cells were then spread onto a TBAB+CM plate. Two colonies from the transformation were streaked onto a TBAB+CM plate for isolation, and each was tested for alpha-L-arabinofuranosidase production.

Colonies were picked and individually grown in 3-5 ml LB medium at 37° C. with shaking at 300 rpm. After growing for 5-6 hours, a 500 µl volume of each culture was inoculated into 50 ml of either Opt-MRS medium or FNL medium in 125 ml plastic non-baffled shake flasks. The shake flasks were incubated at 37° C. for 72 hours at 250 rpm. The broths were harvested and pelleted at 3100×g for 35 minutes.

Fifty µl of a 50% slurry of HisLink™ Protein Purification Resin (Promega Corporation) per ml of broth were added to each cell-free broth in Falcon® tubes. The mixtures were incubated on a rotating rotisserie or with a stir bar at 4° C. overnight. After incubation, the tubes were placed in an upright rack to allow the resin to settle for approximately 5 minutes. Each supernatant was removed, leaving undisturbed the resin with residual supernatant. Each bound resin was transferred via pipette to a well of a NUNC® filter plate with a 1.5 ml wash plate attached below, and the resin was allowed to settle for 3 minutes. Supernatants were removed and discarded via pipetting. One ml of wash buffer (20 mM Tris-HCl, pH 8.0 with 5 mM imidazole) was forcefully added to each well to ensure that the resin was covered with the wash buffer. The resin was allowed to settle for 3 minutes. The supernatants were removed and discarded via pipetting while leaving the resin untouched. After removing the wash buffer, the wash plate was detached and bottom holes of the wells in use were sealed. One ml of elution buffer (20 mM Tris-HCl, pH 8.0 with 250 mM imidazole) was added to the resin in each well and the wells were then sealed on top as well. The plate was incubated in a 4° C. rotisserie for 2 hours. Top and bottom seals were removed and a fresh collection plate was attached to the filter plate. Both plates were centrifuged for 30 seconds up to 1000 rpm until all liquid had flowed through into the collection plate. Eluates were transferred from the collection plate to Eppendorf tubes.

Five µl aliquots of each sample of pEbZn184ND were added to 10 µl aliquots of SDS-PAGE sample buffer (Bio-Rad Laboratories, Inc.) and incubated for 10 minutes at 98° C. using a thermocycler. A pre-cast SDS-PAGE 8-16% gel (Bio-Rad Laboratories, Inc.) was run for 30 minutes at 300 volts. A band of approximately the expected molecular mass of 34 kDa was obtained.

Example 7: Genome Sequencing of *Streptomyces thermoalcalitolerans*

The type strain of the species *Streptomyces thermoalcalitolerans* was obtained from the German collection of Microorganisms and Cell Cultures (DSMZ) as DSM 41741 type strain of *Streptomyces thermoalcalitolerans*. The strain was originally isolated from garden soil in Yogyakarta, Indonesia (Kim et al., 1999, *Int. J. Syst. Bacteriol.* 49: 7-17). Chromosomal DNA from a pure culture was purified and subjected to full genome sequencing by Fasteris SA (Switzerland) using Illumina technology. The assembled genome sequence and subsequent analysis of the 16S ribosomal subunit gene sequences confirmed the identity of the strain as *Streptomyces thermoalcalitolerans*. Genes encoding glycoside hydrolases were identified by bioinformatic genome annotation. Genes specifically encoding alpha-L-arabinofuranosidases of glycoside hydrolase family 62 were additionally identified by BLAST similarity searching.

Example 8: Characterization of Genomic DNA from *Streptomyces thermoalcalitolerans* Encoding a GH62 Alpha-L-Arabinofuranosidase The genomic DNA sequence and deduced amino acid sequence of a GH62 alpha-L-arabinofuranosidase coding sequence from *Streptomyces thermoalcalitolerans* are shown in SEQ ID NO: 3 and SEQ ID NO: 4, respectively. The coding sequence is 1428 bp including the stop codon. Using the SignalP 4.0 program (Petersen et al., 2011, *Nature Methods* 8: 785-786), a signal peptide of 36 amino acids was predicted. The predicted mature protein contains 439 amino acids with a predicted molecular mass of 47.1 kDa and a predicted isoelectric point of 6.6. A carbohydrate binding module from CBM family 13 is present from approximately amino acids 37 to 165 of the full-length polypeptide. The GH62 catalytic domain extends from approximately amino acid 173 to 475 of the full-length polypeptide.

A comparative pairwise global alignment of amino acid sequences was determined using the Needleman and Wunsch algorithm (Needleman and Wunsch, 1970, *J. Mol. Biol.* 48: 443-453) with a gap open penalty of 10, a gap extension penalty of 0.5, and the EBLOSUM62 matrix. The alignment showed that the deduced amino acid sequence of the *Actinomadura rubrobrunea* genomic DNA encoding a GH62 alpha-L-arabinofuranosidase shares 91.1% identity (excluding gaps) to the deduced amino acid sequence of a GH62 alpha-L-arabinofuranosidase from *Streptomyces davawensis* (UNIPROT:K4QV65).

Example 9: Construction of Plasmid pEbZn188ND

A synthetic gene coding for the mature polypeptide of the *Streptomyces thermoalcalitolerans* GH62 alpha-L-arabinofuranosidase of SEQ ID NO: 8 was optimized for expression in *Bacillus subtilis* using GeneArt® GeneOptimzer® software and synthesized by Life Technologies. The optimized sequence is shown in SEQ ID NO: 6. The synthetic DNA was subcloned into plasmid pTH295. This was accomplished by digesting pTH295 with Kpn I and Mlu I to remove the multiple cloning site and the *C. cellulovorans* EngE dockerin gene. The synthetic DNA was amplified by PCR using the primers shown below designed to amplify the gene and add regions of identity to the pTH295 vector and a His-6 tag downstream of the synthetic gene coding sequence.

```
Forward primer:
                               (SEQ ID NO: 9)
5'-GTTCATCGATCGCATCGGCTGGCGATACATGCAGCCTG-3'

Reverse primer:
                               (SEQ ID NO: 10)
5'-GTTTTTTATTGATTAACGCGTTTAGTGATGGTGATGGTGA
TGTGAGCCACCGCCTCCTCTTTGTGTCAGCAGTC-3'
```

A total of 50 picomoles of each of the primers above were used in an amplification reaction containing 100 ng of synthetic DNA, 1×HF Buffer (Thermo Fisher Scientific), 2 µl of a blend of dATP, dTTP, dGTP, and dCTP, each at 10 mM, and 1 µl of Phusion polymerase (Thermo Fisher Scientific) in a final volume of 100 µl. The amplification reaction was performed in a thermocycler programmed for 1 cycle at 98° C. for 30 seconds; and 30 cycles each at 98° C. for 5 seconds, 62° C. for 30 seconds, and 72° C. for 30 seconds. After the 30 cycles, the reaction was heated for 10 minutes at 72° C. The heat block then went to a 12° C. soak cycle. The PCR product was isolated by 1.0% agarose gel electrophoresis using TAE buffer where a 909 bp band was excised from the gel and extracted using an Agarose Gel Purification Kit (Clontech Laboratories, Inc.) according to the manufacturer's instructions.

The homologous ends of the PCR product and plasmid pTH295, digested with Kpn I and Mlu I, were joined using an IN-FUSION™ Advantage PCR Cloning Kit (Clontech Laboratories, Inc.). A total of 185 ng of the PCR product and 183 ng of plasmid pTH295 (digested with Kpn I and Mlu I) were used in a reaction containing 2 µl of 5× IN-FUSION™ reaction buffer (Clontech Laboratories, Inc.) and 1 µl of IN-FUSION™ enzyme (Clontech Laboratories, Inc.) in a final volume of 10 µl. The reaction was incubated at 37° C. for 15 minutes, followed by 15 minutes at 50° C., and then placed on ice. A 2.5 µl volume of the reaction was used to transform E. coli STELLAR® Cells according to the manufacturer's instructions. Transformants were selected on 2×YT+Amp plates and the selected transformants were grown overnight in 3 ml of LB+Amp medium at 37° C. Plasmid DNA from several of the resulting E. coli transformants was prepared using a BIOROBOT® 9600. Verification of insertion of the PCR product into the vector was confirmed by digesting with Sac I and Not I. A plasmid showing the correct insert was designated pEbZn188ND.

Example 10: Expression of a Streptomyces thermoalcalitolerans GH62 Alpha-L-Arabinofuranosidase Plasmid pEbZn188ND was transformed into Bacillus subtilis strain IH14 as follows. One µg of plasmid pEbZn188ND was linearized with Sal I. Competent cells of B. subtilis IH14 were prepared according to Anagnostopoulos and Spizizen, 1961, Journal of Bacteriology 81: 741-746. Cells were then centrifuged at 3836×g for 10 minutes. Eighteen ml of cell supernatant were added to 2 ml glycerol. The cell pellet was resuspended in the supernatant/glycerol mixture, distributed in 0.5 ml aliquots, and frozen for storage at −80° C.

A 0.5 ml volume of Spizizen II medium with 2 mM EGTA was added to 0.5 ml of the frozen competent B. subtilis IH14 cells. The cells were thawed in a water bath at 37° C. and divided into 18 tubes (approximately 50 µl each). One µg of linearized plasmid DNA was added to an aliquot of the competent cells and induced with 0.5 ml of chloramphenicol at a final concentration of 0.2 µg per ml. Transformation reactions were incubated at 37° C. for 1 hour with shaking at 250 rpm. Cells were then spread onto a TBAB+CM plate and incubated overnight at 37° C. Two colonies from the transformation were streaked onto a TBAB+CM plate for isolation, and each was tested for alpha-L-arabinofuranosidase production.

Colonies were picked and individually grown in 3-5 ml of LB medium at 37° C. with shaking at 300 rpm. After growing for 5-6 hours, a 500 µl volume of each culture was inoculated into 50 ml of either Opt-MRS medium or FNL medium in 125 ml plastic non-baffled shake flasks. The shake flasks were incubated at 37° C. for 72 hours with shaking at 250 rpm. Broths were harvested and pelleted at 3100×g for 35 minutes.

Fifty µl of a 50% slurry of HisLink™ Protein Purification Resin (Promega Corporation) per ml of broth were added to each cell-free broth in Falcon® tubes. The mixtures were incubated on a rotating rotisserie or with a stir bar at 4° C. overnight. After incubation, the tubes were placed in an upright rack to allow the resin to settle for approximately 5 minutes. Each supernatant was removed, leaving undisturbed the resin with residual supernatant. Each bound resin was transferred via pipette to a well of a NUNC® filter plate with a 1.5 ml wash plate attached below, and the resin was allowed to settle for 3 minutes. Supernatants were removed and discarded via pipetting. One ml of wash buffer (20 mM Tris-HCl, pH 8.0 with 5 mM imidazole) was forcefully added to each well to ensure that the resin was covered with the wash buffer. The resin was allowed to settle for 3 minutes. The supernatants were removed and discarded via pipetting while leaving the resin untouched. After removing the wash buffer, the wash plate was detached and bottom holes of the wells in use were sealed. One ml of elution buffer (20 mM Tris-HCl, pH 8.0 with 250 mM imidazole) was added to the resin in each well and the wells were then sealed on top as well. The plate was incubated in a 4° C. rotisserie for 2 hours. Top and bottom seals were removed and a fresh collection plate was attached to the filter plate. Both plates were centrifuged for 30 seconds up to 1000 rpm until all liquid had flowed through into the collection plate. Eluates were transferred from the collection plate to Eppendorf tubes.

Five µl aliquots of each sample of pEbZn188ND were added to 10 µl aliquots of SDS-PAGE sample buffer and incubated for 10 minutes at 98° C. using a thermocycler. Pre-cast SDS-PAGE 8-16% Gel (Bio-Rad, Hercules Laboratories, Inc.) was run for 30 minutes at 300 volts. A band of approximately the expected molecular mass of 34 kDa was obtained.

Example 11: pH and Temperature Activity Profiles of Actinomadura rubrobrunea Alpha-L-Arabinofuranosidase (EbZn184ND) and Streptomyces thermoalcalitolerans Alpha-L-Arabinofuranosidase (EbZn188ND)

Alpha-L-arabinofuranosidase activity was determined by incubating 50 µl of diluted enzyme solution with 50 µl of 0.5% w/v p-nitrophenyl-α-L-arabinofuranoside (Sigma-Aldrich) prepared in 50 mM phosphoric acid, 50 mM glacial acetic acid, 50 mM boric acid, 0.01% TRITON® X-100, pH 6.0 w/NaOH) at 50° C. for 30 minutes. Then 100 µl of stop solution (0.5 M glycine-NaOH pH10, 2 mM EDTA) were added to stop the reaction and allowed to sit at room temperature for 15 minutes. After centrifugation, the supernatant was then transferred to a new 96-well assay plate for A405 measurement in a SpectraMax M5 Plate Reader (VWR International). pNP-nitrophenol (Sigma-Aldrich) was used as the standard for the assay. The protein concentration of Ni-NTA purified Actinomadura rubrobrunea alpha-L-arabinofuranosidase (EbZn184ND) and Streptomyces thermoalcalitolerans alpha-L-arabinofuranosidase (EbZn188ND) was determined by absorbance spectroscopy at 280 nm (Grimsley et al., 2003, Current Protocols in Protein Science 3.1.1-3.1.9) using a NanoDrop 2000 (Thermo Fisher Scientific).

Figure 2:
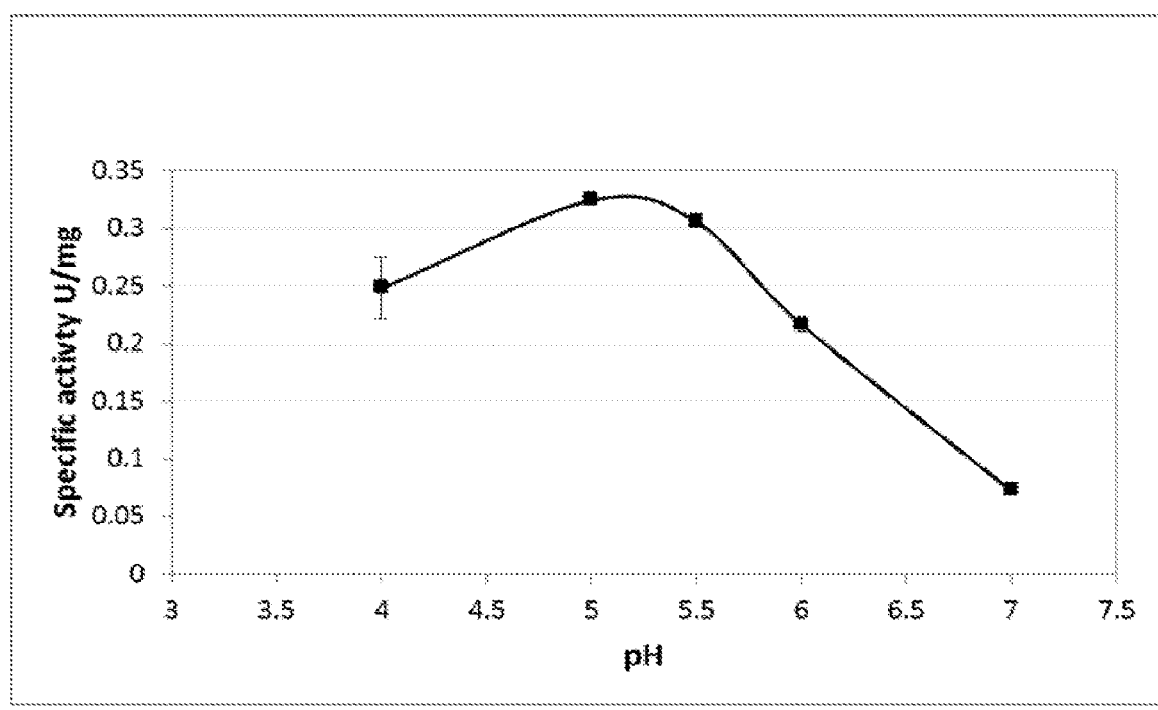
FIG. 2 shows the pH activity profile of a *Streptomyces thermoalcalitolerans* alpha-L-arabinofuranosidase (EbZn188ND) at 50° C.

The pH optima of the A. rubrobrunea GH62 alpha-L-arabinofuranosidase (EbZn184ND) and S. thermoalcalitolerans alpha-L-arabinofuranosidase (EbZn188ND) were determined at pHs from 4.0 and 7.0 at 50° C. The protein was diluted 100 or 200 times with 50 mM phosphoric acid, 50 mM glacial acetic acid, 50 mM boric acid, 0.01% TRITON® X-100 buffer adjusted to desired pHs. According to the results (FIG. 1 and FIG. 2), both EbZn184ND and EbZn188ND had a pH optimum at pH 5.0.

Figure 3:
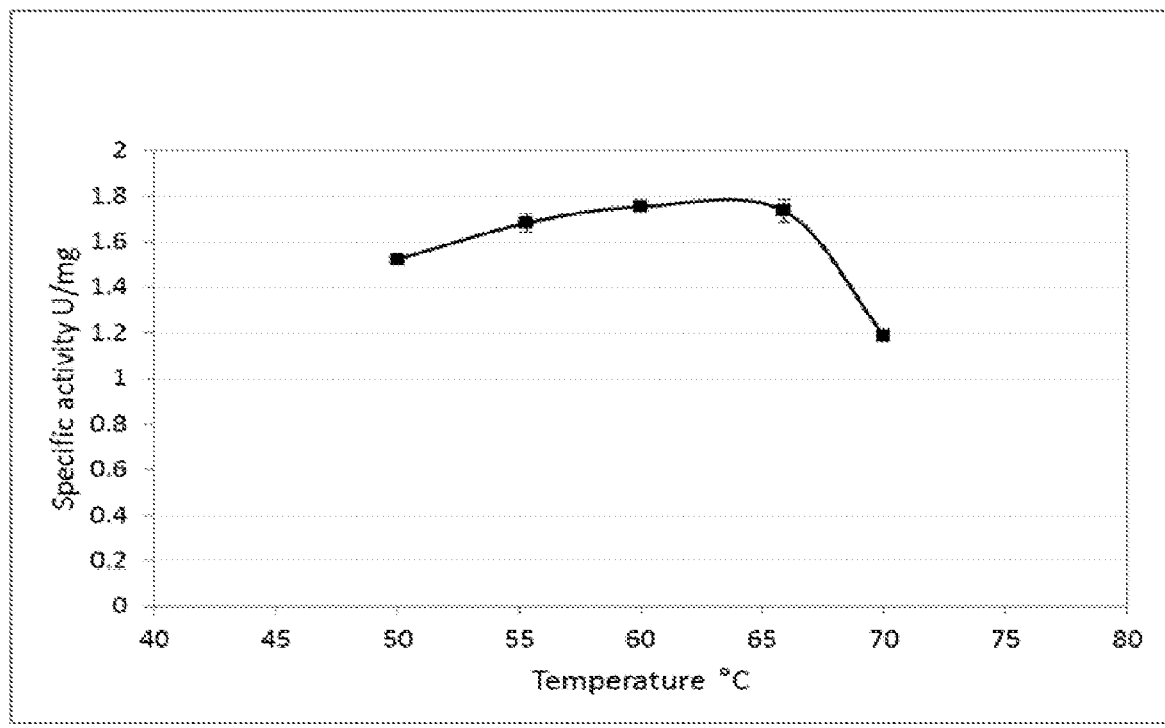
FIG. 3 shows the temperature activity profile of an *Actinomadura rubrobrunea* alpha-L-arabinofuranosidase (EbZn184ND) at pH 5.0.
Figure 4:
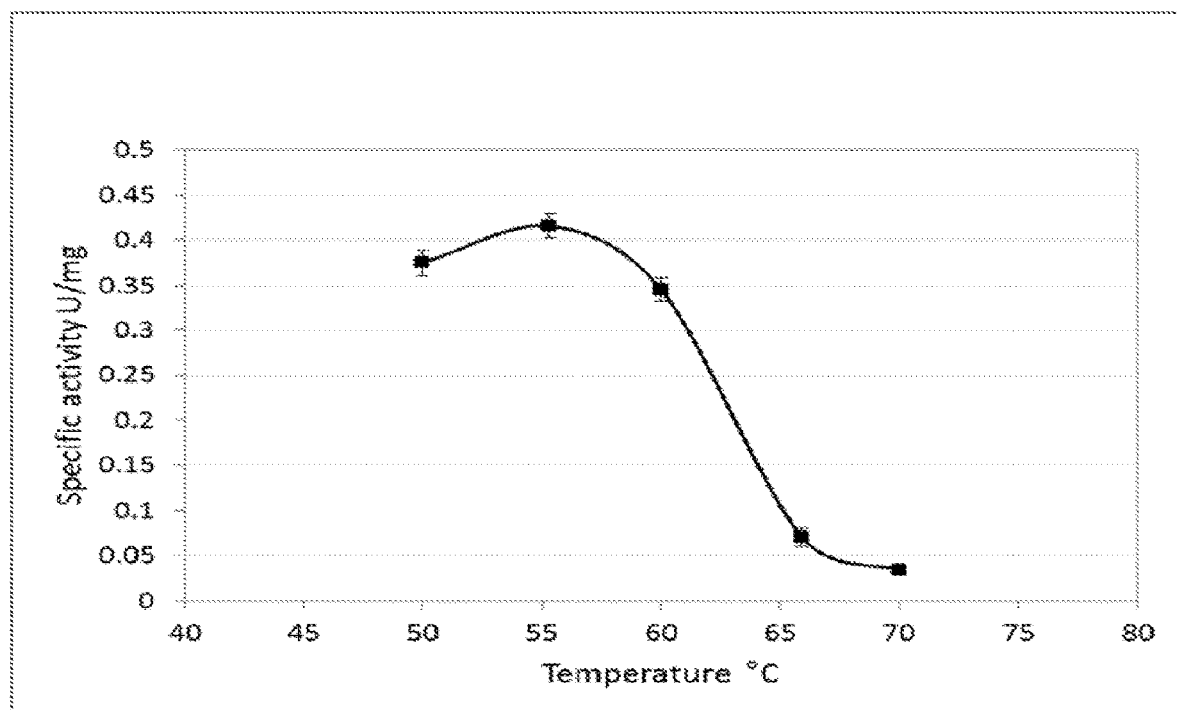
FIG. 4 shows the temperature activity profile of a *Streptomyces thermoalcalitolerans* alpha-L-arabinofuranosidase (EbZn188ND) at pH 5.0.

The temperature optima of the A. rubrobrunea GH62 alpha-L-arabinofuranosidase (EbZn184ND) and S. thermoalcalitolerans alpha-L-arabinofuranosidase (EbZn188ND) were determined from 50° C. to 70° C. at their optimum of pH 5.0. The protein was diluted 100 or 200 times with 50 mM phosphoric acid, 50 mM glacial acetic acid, 50 mM boric acid, 0.01% TRITON® X-100 buffer, pH 5.0. The results (FIG. 3 and FIG. 4) showed that the optimal temperature for GH62 alpha-L-arabinofuranosidase (EbZn184ND) was 65° C. and 55° C. for GH62 alpha-L-arabinofuranosidase (EbZn188ND).

The specific activities of the *A. rubrobrunea* GH62 alpha-L-arabinofuranosidase (EbZn184ND) and *S. thermoalcalitolerans* alpha-L-arabinofuranosidase (EbZn188ND) at their optimal pH and temperature are summarized in Table 1.

TABLE 1

Specific activity of EbZn184ND and EbZn188ND at their optimal conditions

| | U*/mg |
|---|---|
| *A. rubrobrunea* alpha-L-arabinofuranosidase at 65° C., pH 5.0 | 1.75 |
| *S. thermoalcalitolerans* alpha-L-arabinofuranosidase at 55° C., pH 5.0 | 0.42 |

*U is μmole pNP released per minute

The present invention is further described by the following numbered paragraphs:

[1] An isolated polypeptide having arabinofuranosidase activity, selected from the group consisting of: (a) a polypeptide having at least 90% sequence identity to SEQ ID NO: 2 or 92% sequence identity to the mature polypeptide of SEQ ID NO: 4; (b) a polypeptide encoded by a polynucleotide that hybridizes under very high stringency conditions with SEQ ID NO: 1 or the mature polypeptide coding sequence of SEQ ID NO: 3, or the full-length complement thereof; (c) a polypeptide encoded by a polynucleotide having at least 90% sequence identity to SEQ ID NO: 1 or at least 92% sequence identity to the mature polypeptide coding sequence of SEQ ID NO: 3; (d) a variant of SEQ ID NO: 2 or the mature polypeptide of SEQ ID NO: 4 comprising a substitution, deletion, and/or insertion at one or more positions; and (e) a fragment of the polypeptide of (a), (b), (c), or (d) that has arabinofuranosidase activity.

[2] The polypeptide of paragraph 1, having at least 90%, at least 91%, at least 92%, at least 93%, at least 94%, at least 95%, at least 96%, at least 97%, at least 98%, at least 99% or 100% sequence identity to SEQ ID NO: 2 or at least 92%, at least 93%, at least 94%, at least 95%, at least 96%, at least 97%, at least 98%, at least 99% or 100% sequence identity to the mature polypeptide of SEQ ID NO: 4.

[3] The polypeptide of paragraph 1 or 2, which is encoded by a polynucleotide that hybridizes under very high stringency conditions with SEQ ID NO: 1 or the mature polypeptide coding sequence of SEQ ID NO: 3, or the full-length complement thereof.

[4] The polypeptide of any one of paragraphs 1-3, which is encoded by a polynucleotide having at least 90%, at least 91%, at least 92%, at least 93%, at least 94%, at least 95%, at least 96%, at least 97%, at least 98%, at least 99% or 100% sequence identity to SEQ ID NO: 1 or at least 92%, at least 93%, at least 94%, at least 95%, at least 96%, at least 97%, at least 98%, at least 99% or 100% sequence identity to the mature polypeptide coding sequence of SEQ ID NO: 3.

[5] The polypeptide of any one of paragraphs 1-4, comprising or consisting of SEQ ID NO: 2 or SEQ ID NO: 4 or the mature polypeptide of SEQ ID NO: 4.

[6] The polypeptide of paragraph 5, wherein the mature polypeptide is amino acids 37 to 475 of SEQ ID NO: 4.

[7] The polypeptide of any one of paragraphs 1-4, which is a variant of SEQ ID NO: 2 or the mature polypeptide of SEQ ID NO: 4 comprising a substitution, deletion, and/or insertion at one or more positions.

[8] The polypeptide of paragraph 1, which is a fragment of SEQ ID NO: 2 or SEQ ID NO: 4, wherein the fragment has arabinofuranosidase activity.

[9] An isolated polypeptide comprising a catalytic domain selected from the group consisting of: (a) a catalytic domain having at least 90% sequence identity to amino acids 4 to 303 of SEQ ID NO: 2 or amino acids 173 to 475 of SEQ ID NO: 4; (b) a catalytic domain encoded by a polynucleotide that hybridizes under very high stringency conditions with nucleotides 10 to 909 of SEQ ID NO: 1 or nucleotides 517 to 1425 of SEQ ID NO: 3, or the full-length complement thereof; (c) a catalytic domain encoded by a polynucleotide having at least 90% sequence identity to nucleotides 10 to 909 of SEQ ID NO: 1 or at least 92% sequence identity to nucleotides 517 to 1425 of SEQ ID NO: 3; (d) a variant of amino acids 4 to 303 of SEQ ID NO: 2 or amino acids 173 to 475 of SEQ ID NO: 4 comprising a substitution, deletion, and/or insertion at one or more positions; and (e) a fragment of the catalytic domain of (a), (b), (c), or (d) that has arabinofuranosidase activity.

[10] The polypeptide of paragraph 9, further comprising a carbohydrate binding module.

[11] An isolated polypeptide comprising a carbohydrate binding module operably linked to a catalytic domain, wherein the binding domain is selected from the group consisting of: (a) a carbohydrate binding module having at least 92% sequence identity to amino acids 37 to 165 of SEQ ID NO: 4; (b) a carbohydrate binding module encoded by a polynucleotide that hybridizes under very high stringency conditions with nucleotides 109 to 495 of SEQ ID NO: 3 or the full-length complement thereof; (c) a carbohydrate binding module encoded by a polynucleotide having at least 92% sequence identity to nucleotides 109 to 495 of SEQ ID NO 3; (d) a variant of amino acids 37 to 165 of SEQ ID NO: 4 comprising a substitution, deletion, and/or insertion at one or more positions; and (e) a fragment of (a), (b), (c), (d) or (e) that has carbohydrate binding activity.

[12] The polypeptide of paragraph 11, wherein the catalytic domain is obtained from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

[13] A composition comprising the polypeptide of any one of paragraphs 1-12.

[14] A whole broth formulation or cell culture composition comprising the polypeptide of any one of paragraphs 1-12.

[15] An isolated polynucleotide encoding the polypeptide of any one of paragraphs 1-12.

[16] A nucleic acid construct or expression vector comprising the polynucleotide of paragraph 15 operably linked to one or more control sequences that direct the production of the polypeptide in an expression host.

[17] A recombinant host cell transformed with the polynucleotide of paragraph 15 operably linked to one or more control sequences that direct the production of the polypeptide.

[18] A method of producing the polypeptide of any one of paragraphs 1-12, comprising cultivating a wild-type cell under conditions conducive for production of the polypeptide.

[19] The method of paragraph 18, further comprising recovering the polypeptide.

[20] A method of producing a polypeptide having arabinofuranosidase activity, comprising cultivating the recombinant host cell of paragraph 17 under conditions conducive for production of the polypeptide.

[21] The method of paragraph 20, further comprising recovering the polypeptide.

[22] A transgenic plant, plant part or plant cell transformed with a polynucleotide encoding the polypeptide of any one of paragraphs 1-12.

[23] A method of producing a polypeptide having arabinofuranosidase activity, comprising cultivating the transgenic plant or plant cell of paragraph 22 under conditions conducive for production of the polypeptide.

[24] The method of paragraph 23, further comprising recovering the polypeptide.

[25] An isolated polynucleotide encoding a signal peptide comprising or consisting of amino acids 1 to 24 of SEQ ID NO: 2 or amino acids 1 to 36 of SEQ ID NO: 4.

[26] A nucleic acid construct or expression vector comprising a gene encoding a protein operably linked to the polynucleotide of paragraph 25, wherein the gene is foreign to the polynucleotide encoding the signal peptide.

[27] A recombinant host cell comprising a gene encoding a protein operably linked to the polynucleotide of paragraph 25, wherein the gene is foreign to the polynucleotide encoding the signal peptide.

[28] A method of producing a protein, comprising cultivating a recombinant host cell comprising a gene encoding a protein operably linked to the polynucleotide of paragraph 25, wherein the gene is foreign to the polynucleotide encoding the signal peptide, under conditions conducive for production of the protein.

[29] The method of paragraph 28, further comprising recovering the protein.

[30] A process for degrading a cellulosic or hemicellulosic material, comprising: treating the cellulosic or hemicellulosic material with an enzyme composition comprising the polypeptide having arabinofuranosidase activity of any one of paragraphs 1-12.

[31] The process of paragraph 30, wherein the cellulosic or hemicellulosic material is pretreated.

[32] The process of paragraph 30 or 31, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[33] The process of paragraph 32, wherein the cellulase is one or more enzymes selected from the group consisting of an endoglucanase, a cellobiohydrolase, and a beta-glucosidase.

[34] The process of paragraph 32, wherein the hemicellulase is one or more enzymes selected from the group consisting of a xylanase, an acetylxylan esterase, a feruloyl esterase, an arabinofuranosidase, a xylosidase, and a glucuronidase.

[35] The process of any one of paragraphs 30-34, further comprising recovering the degraded cellulosic or hemicellulosic material.

[36] The process of paragraph 35, wherein the degraded cellulosic or hemicellulosic material is a sugar.

[37] The process of paragraph 36, wherein the sugar is selected from the group consisting of glucose, xylose, mannose, galactose, and arabinose.

[38] A process for producing a fermentation product, comprising: (a) saccharifying a cellulosic or hemicellulosic material with an enzyme composition comprising the polypeptide having xylanase activity of any one of paragraphs 1-12; (b) fermenting the saccharified cellulosic or hemicellulosic material with one or more fermenting microorganisms to produce the fermentation product; and (c) recovering the fermentation product from the fermentation.

[39] The process of paragraph 38, wherein the cellulosic or hemicellulosic material is pretreated.

[40] The process of paragraph 38 or 39, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[41] The process of paragraph 40, wherein the cellulase is one or more enzymes selected from the group consisting of an endoglucanase, a cellobiohydrolase, and a beta-glucosidase.

[42] The process of paragraph 40, wherein the hemicellulase is one or more enzymes selected from the group consisting of a xylanase, an acetylxylan esterase, a feruloyl esterase, an arabinofuranosidase, a xylosidase, and a glucuronidase.

[43] The process of any one of paragraphs 38-42, wherein steps (a) and (b) are performed simultaneously in a simultaneous saccharification and fermentation.

[44] The process of any one of paragraphs 38-43, wherein the fermentation product is an alcohol, an alkane, a cycloalkane, an alkene, an amino acid, a gas, isoprene, a ketone, an organic acid, or polyketide.

[45] A process of fermenting a cellulosic or hemicellulosic material, comprising: fermenting the cellulosic or hemicellulosic material with one or more fermenting microorganisms, wherein the cellulosic or hemicellulosic material is saccharified with an enzyme composition comprising the polypeptide having arabinofuranosidase activity of any one of paragraphs 1-12.

[46] The process of paragraph 45, wherein the cellulosic or hemicellulosic material is pretreated before saccharification.

[47] The process of paragraph 45 or 46, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[48] The process of paragraph 47, wherein the cellulase is one or more enzymes selected from the group consisting of an endoglucanase, a cellobiohydrolase, and a beta-glucosidase.

[49] The process of paragraph 47, wherein the hemicellulase is one or more enzymes selected from the group consisting of a xylanase, an acetylxylan esterase, a feruloyl esterase, an arabinofuranosidase, a xylosidase, and a glucuronidase.

[50] The process of any one of paragraphs 45-49, wherein the fermenting of the cellulosic or hemicellulosic material produces a fermentation product.

[51] The process of paragraph 50, further comprising recovering the fermentation product from the fermentation.

[52] The process of paragraph 50 or 51, wherein the fermentation product is an alcohol, an alkane, a cycloalkane, an alkene, an amino acid, a gas, isoprene, a ketone, an organic acid, or polyketide.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a polypeptide having arabinofuranosidase activity, wherein the polynucleotide is operably linked to one or more heterologous control sequences that direct the production of the polypeptide in a recombinant host cell, and wherein the polypeptide having arabinofuranosidase activity is selected from the group consisting of:
   (a) a polypeptide having at least 95% sequence identity to SEQ ID NO: 2 or amino acids 37 to 475 of SEQ ID NO: 4;
   (b) a polypeptide encoded by a polynucleotide having at least 95% sequence identity to SEQ ID NO: 1 or nucleotides 109 to 1425 of SEQ ID NO: 3;
   (c) a fragment of the polypeptide of (a) or (b), wherein the fragment has arabinofuranosidase activity;
   (d) a polypeptide comprising a catalytic domain having at least 95% sequence identity to amino acids 4 to 303 of SEQ ID NO: 2 or amino acids 173 to 475 of SEQ ID NO: 4;
   (e) a polypeptide comprising a catalytic domain encoded by a polynucleotide having at least 95% sequence identity to nucleotides 10 to 909 of SEQ ID NO: 1 or nucleotides 517 to 1425 of SEQ ID NO: 3; and
   (f) a fragment of the catalytic domain of (d) or (e), wherein the fragment has arabinofuranosidase activity.

2. A recombinant host cell transformed with the nucleic acid construct of claim 1.

3. A method of producing a polypeptide having arabinofuranosidase activity, comprising cultivating the recombinant host cell of claim 2 under conditions conducive for production of the polypeptide, and optionally recovering the polypeptide.

4. The nucleic acid construct of claim 1, wherein the polypeptide having arabinofuranosidase activity has at least 96% sequence identity to SEQ ID NO: 2 or amino acids 37 to 475 of SEQ ID NO: 4.

5. The nucleic acid construct of claim 1, wherein the polypeptide having arabinofuranosidase activity has at least 97% sequence identity to SEQ ID NO: 2 or amino acids 37 to 475 of SEQ ID NO: 4.

6. The nucleic acid construct of claim 1, wherein the polypeptide having arabinofuranosidase activity has at least 98% sequence identity to SEQ ID NO: 2 or amino acids 37 to 475 of SEQ ID NO: 4.

7. The nucleic acid construct of claim 1, wherein the polypeptide having arabinofuranosidase activity has at least 99% sequence identity to SEQ ID NO: 2 or amino acids 37 to 475 of SEQ ID NO: 4.

8. The nucleic acid construct of claim 1, wherein the polypeptide having arabinofuranosidase activity comprises SEQ ID NO: 2.

9. The nucleic acid construct of claim 1, wherein the polypeptide having arabinofuranosidase activity comprises SEQ ID NO: 4 or amino acids 37 to 475 of SEQ ID NO: 4.

10. The nucleic acid construct of claim 1, wherein the polypeptide comprising a catalytic domain having arabinofuranosidase activity has at least 96% sequence identity to amino acids 4 to 303 of SEQ ID NO: 2 or amino acids 173 to 475 of SEQ ID NO: 4.

11. The nucleic acid construct of claim 1, wherein the polypeptide comprising a catalytic domain having arabinofuranosidase activity has at least 97% sequence identity to amino acids 4 to 303 of SEQ ID NO: 2 or amino acids 173 to 475 of SEQ ID NO: 4.

12. The nucleic acid construct of claim 1, wherein the polypeptide comprising a catalytic domain having arabinofuranosidase activity has at least 98% sequence identity to amino acids 4 to 303 of SEQ ID NO: 2 or amino acids 173 to 475 of SEQ ID NO: 4.

13. The nucleic acid construct of claim 1, wherein the polypeptide comprising a catalytic domain having arabinofuranosidase activity has at least 99% sequence identity to amino acids 4 to 303 of SEQ ID NO: 2 or amino acids 173 to 475 of SEQ ID NO: 4.

14. The nucleic acid construct of claim 1, wherein the polypeptide comprising a catalytic domain having arabinofuranosidase activity comprises amino acids 4 to 303 of SEQ ID NO: 2.

15. The nucleic acid construct of claim 1, wherein the polypeptide comprising a catalytic domain having arabinofuranosidase activity comprises amino acids 173 to 475 of SEQ ID NO: 4.

16. The nucleic acid construct of claim 1, wherein the polypeptide comprising the catalytic domain further comprises a carbohydrate binding module.

17. A nucleic acid construct comprising a polynucleotide encoding a polypeptide having biological activity comprising a carbohydrate binding module operably linked to a heterologous catalytic domain and one or more control sequences that direct the production of the polypeptide in a recombinant host cell, wherein the carbohydrate binding module is selected from the group consisting of:
(a) a carbohydrate binding module having at least 95% sequence identity to amino acids 37 to 165 of SEQ ID NO: 4;
(b) a carbohydrate binding module encoded by a polynucleotide having at least 95% sequence identity to nucleotides 109 to 495 of SEQ ID NO 3; and
(c) a fragment of (a) or (b), wherein the fragment has carbohydrate binding activity.

18. The nucleic acid construct of claim 17, wherein the catalytic domain is obtained from a hydrolase, isomerase, ligase, lyase, oxidoreductase, or transferase.

19. The nucleic acid construct of claim 17, wherein the carbohydrate binding module has at least 96% sequence identity to amino acids 37 to 165 of SEQ ID NO: 4.

20. The nucleic acid construct of claim 17, wherein the carbohydrate binding module has at least 97% sequence identity to amino acids 37 to 165 of SEQ ID NO: 4.

21. The nucleic acid construct of claim 17, wherein the carbohydrate binding module has at least 98% sequence identity to amino acids 37 to 165 of SEQ ID NO: 4.

22. The nucleic acid construct of claim 17, wherein the carbohydrate binding module has at least 99% sequence identity to amino acids 37 to 165 of SEQ ID NO: 4.

23. The nucleic acid construct of claim 17, wherein the carbohydrate binding module comprises amino acids 37 to 165 of SEQ ID NO: 4.

24. A recombinant host cell transformed with the nucleic acid construct of claim 17.

25. A method of producing a polypeptide, comprising cultivating the recombinant host cell of claim 24 under conditions conducive for production of the polypeptide having biological activity, and optionally recovering the polypeptide having biological activity.

* * * * *